(12) United States Patent
Lu et al.

(10) Patent No.: US 10,473,605 B2
(45) Date of Patent: Nov. 12, 2019

(54) FLUID TESTING SYSTEM

(71) Applicant: Hewlett-Packard Development Company, L.P., Houston, TX (US)

(72) Inventors: Sirena C. Lu, San Diego, CA (US); Melinda M. Valencia, Chula Vista, CA (US); Jeremy Sells, Albany, OR (US); Manish Giri, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 600 days.

(21) Appl. No.: 15/112,743

(22) PCT Filed: Jan. 30, 2015

(86) PCT No.: PCT/US2015/013825
§ 371 (c)(1),
(2) Date: Jul. 20, 2016

(87) PCT Pub. No.: WO2015/116956
PCT Pub. Date: Aug. 6, 2015

(65) Prior Publication Data
US 2016/0334351 A1    Nov. 17, 2016

Related U.S. Application Data

(63) Continuation-in-part of application No. PCT/US2014/013748, filed on Jan. 30, 2014.

(51) Int. Cl.
*G01N 17/00* (2006.01)
*G01N 27/06* (2006.01)
(Continued)

(52) U.S. Cl.
CPC ........ *G01N 27/06* (2013.01); *B01L 3/502715* (2013.01); *G01N 15/0266* (2013.01);
(Continued)

(58) Field of Classification Search
CPC .............. G01N 27/06; G01N 15/0266; G01N 15/1031; G01N 2015/1006;
(Continued)

(56) References Cited

U.S. PATENT DOCUMENTS 4,404,636 A    9/1983 Campbell, Jr.
4,420,720 A    12/1983 Newton et al.
(Continued)

FOREIGN PATENT DOCUMENTS

CN    1916639 A    2/2007
CN    102360025 A    2/2012
(Continued)

OTHER PUBLICATIONS

Minerick, A.R., et al. "Manipulation and characterization of red blood cells with alternating current fields in microdevices". Nov. 6, 2003, Electrophoresis, 24(21), pp. 3703-3717.
(Continued)

*Primary Examiner* — Melissa J Koval
*Assistant Examiner* — Courtney G McDonnough
(74) *Attorney, Agent, or Firm* — Perry + Currier Inc

(57) ABSTRACT

A fluid testing system comprises controlling hardware that serves to control an electric sensor on a fluid testing cassette. In one implementation, the controlling hardware is part of a cassette interface. In another implementation, the controlling hardware is part of the portable electronic device. In one implementation, the fluid testing system applies two different frequencies of alternating current are applied to two different electric sensors.

15 Claims, 10 Drawing Sheets

(51) Int. Cl.
  *G01N 15/02* (2006.01)
  *G01N 15/10* (2006.01)
  *G01N 15/14* (2006.01)
  *G01N 27/12* (2006.01)
  *B01L 3/00* (2006.01)
  *G01N 15/12* (2006.01)

(52) U.S. Cl.
  CPC ......... *G01N 15/1031* (2013.01); *G01N 15/12* (2013.01); *G01N 15/1484* (2013.01); *G01N 27/12* (2013.01); *B01L 2200/10* (2013.01); *B01L 2300/0645* (2013.01); *G01N 2015/1006* (2013.01); *G01N 2015/1493* (2013.01)

(58) Field of Classification Search
  CPC ....... G01N 2015/1493; B01L 3/502715; B01L 2200/10; B01L 2300/0645
  See application file for complete search history.

(56) References Cited

U.S. PATENT DOCUMENTS

| | | | |
|---|---|---|---|
| 5,965,410 A | 10/1999 | Chow et al. | |
| 6,426,615 B1 | 7/2002 | Mehta | |
| 6,437,551 B1 | 8/2002 | Krulevitch et al. | |
| 6,967,489 B2 | 11/2005 | Brooks et al. | |
| 8,390,304 B2 | 3/2013 | Patterson | |
| 8,440,093 B1 | 5/2013 | Nassef et al. | |
| 8,642,287 B2 | 2/2014 | Wang et al. | |
| 8,795,497 B2 | 8/2014 | Sato et al. | |
| 8,841,924 B2 | 9/2014 | Reccius et al. | |
| 9,566,581 B2 | 2/2017 | Imran | |
| 2002/0081228 A1 | 6/2002 | Hui et al. | |
| 2002/0125959 A1* | 9/2002 | Atsumi | H03L 7/26 331/3 |
| 2003/0094953 A1 | 5/2003 | Brooks et al. | |
| 2003/0148530 A1 | 8/2003 | Lauks | |
| 2004/0227529 A1 | 11/2004 | Brooks et al. | |
| 2005/0114041 A1 | 5/2005 | Gawad | |
| 2005/0118705 A1 | 6/2005 | Rabbitt et al. | |
| 2006/0062074 A1 | 3/2006 | Gundersen et al. | |
| 2008/0221805 A1 | 9/2008 | Andrews | |
| 2009/0212788 A1 | 8/2009 | Patterson | |
| 2010/0006441 A1 | 1/2010 | Renaud et al. | |
| 2010/0025246 A1 | 2/2010 | Cho et al. | |
| 2010/0088039 A1 | 4/2010 | Yang et al. | |
| 2011/0080181 A1* | 4/2011 | Sato | A61B 5/0537 324/692 |
| 2011/0162439 A1* | 7/2011 | Ayliffe | B01L 3/502715 73/61.71 |
| 2011/0275111 A1 | 11/2011 | Pettigrew et al. | |
| 2011/0279130 A1 | 11/2011 | Reccius et al. | |
| 2012/0084022 A1* | 4/2012 | Giovangrandi | G01F 1/58 702/45 |
| 2012/0142032 A1 | 6/2012 | Morgan et al. | |
| 2012/0168309 A1 | 7/2012 | Heikenfeld | |
| 2013/0085680 A1 | 4/2013 | Arlen et al. | |
| 2013/0154671 A1 | 6/2013 | Lee et al. | |
| 2013/0167621 A1 | 7/2013 | Lin et al. | |
| 2013/0193003 A1 | 8/2013 | Reed et al. | |
| 2013/0252234 A1 | 9/2013 | Nassef et al. | |
| 2013/0258318 A1 | 10/2013 | Ayliffe | |
| 2013/0267835 A1* | 10/2013 | Edwards | A61B 5/061 600/424 |
| 2013/0313113 A1 | 11/2013 | Koser | |
| 2014/0004501 A1 | 1/2014 | Talebpour et al. | |
| 2014/0014509 A1* | 1/2014 | Yan | G01N 33/86 204/403.02 |
| 2014/0021105 A1 | 1/2014 | Lee | |
| 2014/0284221 A1 | 9/2014 | Liu et al. | |

FOREIGN PATENT DOCUMENTS

| | | |
|---|---|---|
| CN | 102460114 A | 5/2012 |
| CN | 102460137 A | 5/2012 |
| JP | 2013015498 A | 1/2013 |
| TW | 200305717 A | 11/2003 |
| TW | 201224447 A | 6/2012 |
| WO | WO-2012064878 | 5/2012 |
| WO | WO-2012110922 | 8/2012 |
| WO | WO-2013117233 | 8/2013 |
| WO | WO-2014178827 | 11/2014 |
| WO | WO-2015116083 | 8/2015 |

OTHER PUBLICATIONS

Cheng, X. et al., "Cell detection and counting through cell lysate impedance spectroscopy in microfluidic devices." Lab on a Chip 7, No. 6 (2007): 746-755.

Chin, et al., "Low-cost microdevices for point-of-care testing." In Point-of-care Diagnostics on a chip, pp. 3-21. Springer Berlin Heidelberg, 2013.

Claudel, J. et al., "Microfluidic biosensor for single cell high speed flow impedance spectroscopy." In Proceedings of the 8th International Conference on Sensing Technology, pp. 343-347. 2014.

International Search Report/Written Opinion, dated May 19, 2015, PCT Patent Application No. PCT/US2015/013825.

International Search Report/Written Opinion, dated Oct. 27, 2014, PCT Patent Application No. PCT/US2014/013748.

International Search Report/Written Opinion, dated May 21, 2015. PCT Patent Application No. PCT/US2015/013854.

Daniel Spencer et al: "Positional dependence of particles in microfludic impedance cytometry", Lab on a Chip, vol. 11, No. 7, Jan. 1, 2011 (Jan. 1, 2011), p. 1234, XP055125402, ISSN: 1473-0197, DOI: 10.1039/c11c20016j * Abstract, p. 1236, Col. 2; figures 1, 4 *.

Karen Cheung, Shady Gawad, and Philippe Renaud, "Impedance Spectroscopy Flow Cytometry: On-Chip Label-Free Cell Differentiation", ISAC Cytometry Part 1 65A, 2005.

Tao Sun et al: "Single-cell microfluidic impedance cytometry: a review", Microfluidics and Nanofluidics, Springer, Berlin, DE, vol. 8, No. 4, Mar. 6, 2010 (Mar. 6, 2010), pages.

* cited by examiner

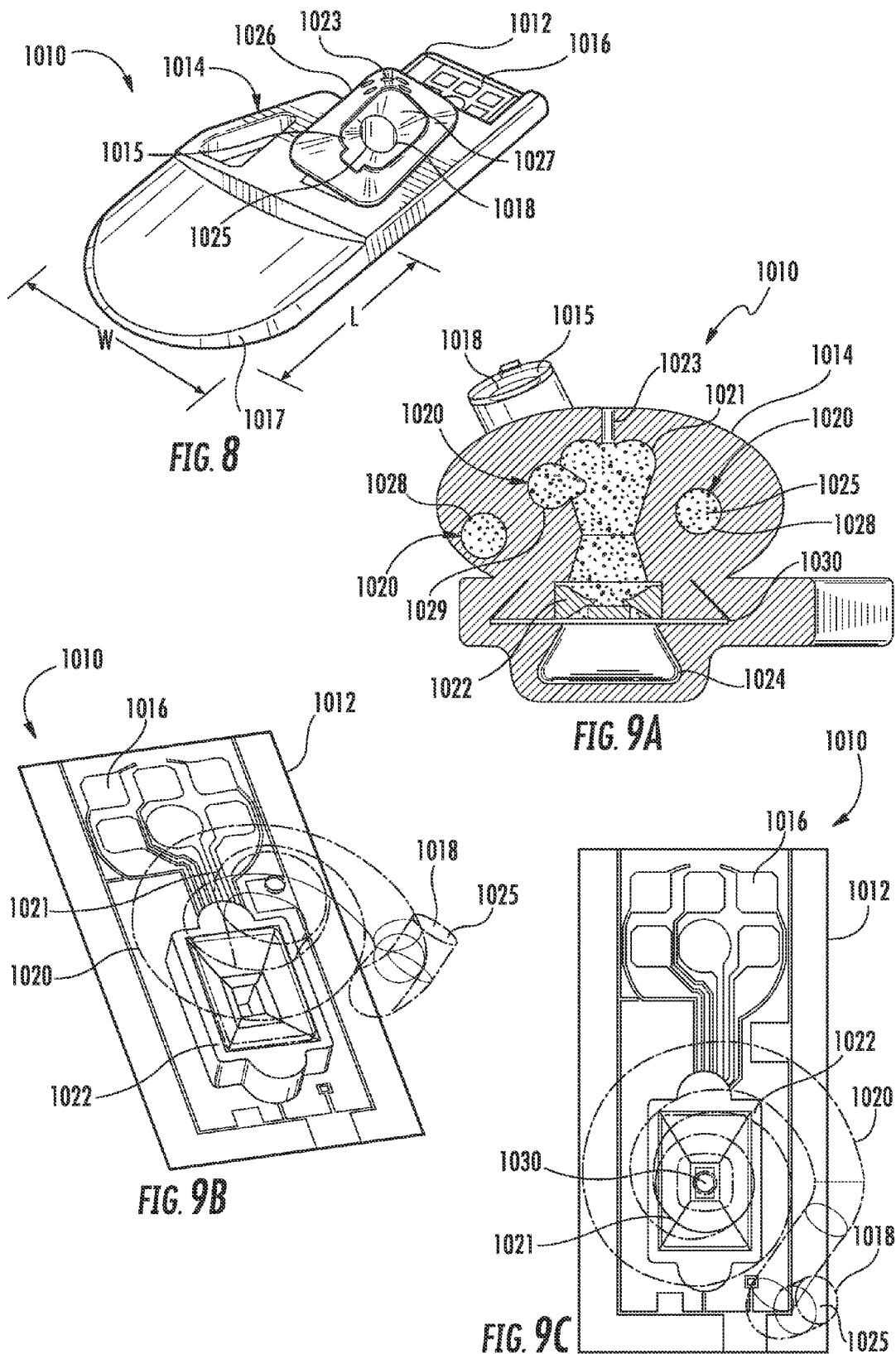

US 10,473,605 B2

FLUID TESTING SYSTEM

CROSS-REFERENCE TO RELATED APPLICATION

This application is a U.S. National Stage Application of International Patent Application No. PCT/US2015/013825, filed on Jan. 30, 2015, and entitled "FLUID TESTING SYSTEM," which claims priority to International Patent Application No. PCT/US2014/013748, filed on Jan. 30, 2014, and entitled "MICROFLUIDIC SENSING DEVICE", hereby incorporated by reference in its entirety.

BACKGROUND

Fluid samples, such as blood samples, are frequently taken and analyzed for clinical diagnostics to identify disease and other health related issues. For such diagnostics, many different tests are performed on the fluid, requiring multiple different fluid samples. For example, such fluid testing frequently involves identification of the size of the cells or particles and identification of the number of such cells or particles. To perform the many different tests often requires multiple different fluid testing systems. Such existing fluid testing systems, such as benchtop testing systems, are large, cumbersome and difficult to use.

BRIEF DESCRIPTION OF THE DRAWINGS

FIG. 8 is a perspective view of an example cassette.

FIG. 9A is a sectional view of the cassette of FIG. 8 with a modified exterior.

FIG. 9B is a perspective view of the cassette of FIG. 9A with portions omitted or shown transparently.

FIG. 9C is a top view of the cassette of FIG. 9A with portions omitted or shown transparently.

DETAILED DESCRIPTION OF EXAMPLES

Figure 1:
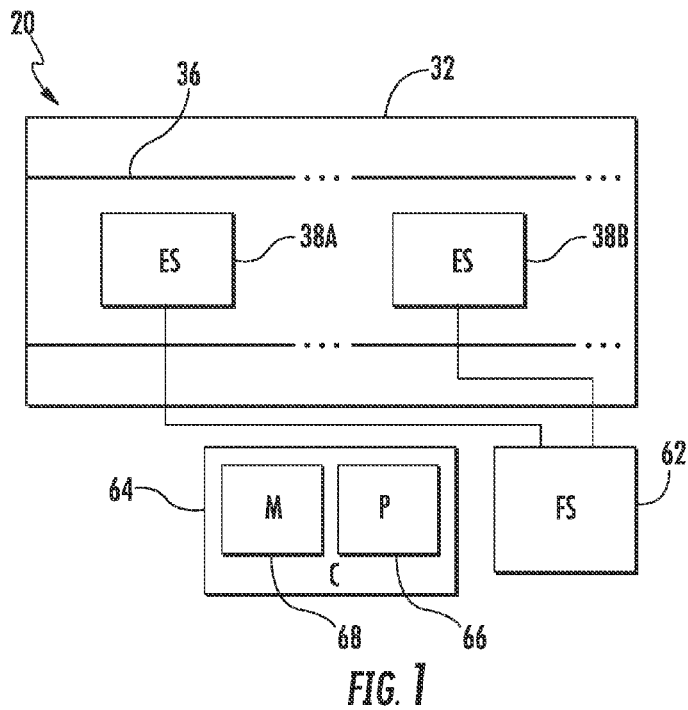
FIG. 1 is a schematic diagram of an example fluid testing system.

FIG. 1 schematically illustrates an example fluid testing system 20. As will be described hereafter, fluid testing system 20 provides a single platform to perform multiple different tests upon a single fluid sample. Because testing system 20 produces data for multiple different characteristics or parameters of the fluid being tested using a single fluid sample, system 20 allows such testing and diagnostics performed with a single testing system. Moreover, testing system 20 reduces a number of fluid samples or blood samples that must be taken and reduces the amount of potentially hazardous medical waste resulting from such testing.

Fluid testing system 20 comprises a substrate 32 in which his formed a microfluidic channel 36, electric sensors 38A, 38B (collectively referred to as electric sensors 38), frequency source 62 and frequency controller 64. Channel 36 comprises a fluidic channel or passage to direct and guide fluid of a fluid sample being tested. In one implementation, channel 36 is formed within a substrate of the microfluidic chip and extends from a reservoir (not shown) to direct portions of the fluid sample across electric sensors 38. In one implementation, channel 36 directs fluid back to the reservoir of the microfluidic chip for circulating fluid. In another implementation, microfluidic channel 36 directs fluid back to a discharge reservoir or discharge port. In yet another implementation, channel 36 extends to other fluid destinations.

Each of electric sensors 38 comprises a microfabricated device formed upon a substrate 32 within channel 36. In the example illustrated, each of sensors 38 comprises a microdevice that is designed to output electrical signals or cause changes in electrical signals that indicate properties, parameters or characteristics of the fluid and/or cells/particles of the fluid passing through channel 36. In the example illustrated, each of sensors 38 comprises an electric sensor which outputs signals based upon changes in electrical impedance brought about by differently sized particles or cells flowing through channel 36 and impacting impedance of the electrical field across or within channel 36. In one implementation, each of sensors 38 comprises an electrically charged highside electrode and an a low side electrode formed within or integrated within a surface of channel 36. In one implementation, the low side electrode is electrically grounded. In another implementation, the low side electrode is electrically floating. Electric sensors 38, to which alternating current is applied, or sufficiently separated physically from one another so as to not infringe on the electric field and the resulting signal of the other. In one implementation, electric sensor 38A outputs signals indicating a number or quantity of cells or particles opposite to sensor 38 are passing across sensor 38 at any moment in time. Electric sensor 38B outputs signals indicating characteristics of such individual cells are particles, such as a size of a cell or particle or the like.

Frequency source 62 comprises at least one source of different non-zero frequencies of alternating current. In one implementation, frequency source 62 comprises an individual frequency source for each of the individual electric sensors 38. In another implementation, frequency source 62 comprises a single frequency source which is selectively applies different non-zero frequencies of alternating current to the different electric sensors 38 or which concurrently supplies different non-zero frequencies of alternating current to the different electric sensors 38.

In one implementation, frequency source 62 comprises a direct digital synthesizer which comprises a frequency reference such as a crystal or surface acoustic wave (SAW) oscillator, a numerically controlled oscillator and a digital to analog converter. In another implementation, frequency source 62 comprises an analog or phase-locked loop (PLL) frequency source. In one implementation, frequency source 62 is designed so as to apply a first lower non-zero frequency of alternating current to electric sensor 38A to facilitate determination of the size of individual cells and to apply a second higher non-zero frequency of alternating current to the electric sensor 38B to facilitate cell membrane capacitance. In one implementation frequency source 62 is designed to apply different non-zero frequencies to facilitate counting of the number of cells or particles passing across each of sensors 38. In one implementation, frequency source 62 applies a first frequency within the range of up to 1 MHz to sensor 38A and applies a second higher frequency greater than 1 MHz and up to 10 MHz.

Frequency controller 64 controls the application of the different non-zero frequencies of alternating current to electric sensors 38. In one implementation, frequency controller 64 facilitate user selection of the different non-zero frequencies of alternating current applied to the different electric sensors 38. Frequency controller 64 comprises processing unit 66 and memory 68. Processing unit follows instructions contained in memory 68 to output control signals directing the operation of frequency source 62. For purposes of this application, the term "processing unit" shall mean a presently developed or future developed processing unit that executes sequences of instructions contained in a memory. Execution of the sequences of instructions causes the processing unit to perform actions such as generating control signals. The instructions may be loaded in a random access memory (RAM) for execution by the processing unit from a read only memory (ROM), a mass storage device, or some other persistent storage or non-transitory computer-readable medium containing program logic or logic encodings. In other implementations, hard wired circuitry may be used in place of or in combination with machine readable instructions to implement the functions described. For example, controller 64 may be embodied as part of application-specific integrated circuits (ASICs). Unless otherwise specifically noted, the controller 64 is not limited to any specific combination of hardware circuitry and machine readable instruction, nor to any particular source for the instructions executed by the processing unit.

Because controller 64 applies different non-zero frequencies of alternating current to the different electric sensors 38, the different electric sensor 38 and perform different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially biohazardous waste is also reduced.

Figure 2:
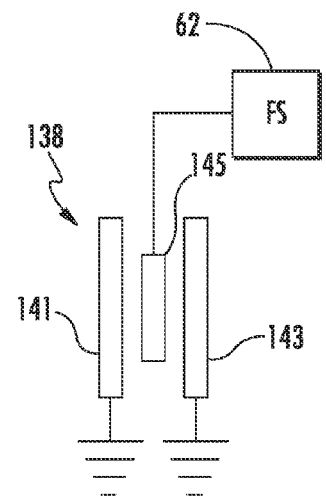
FIG. 2 is a schematic diagram of an example electric sensor of the fluid testing system of FIG. 1.

FIG. 2 schematically illustrates electric sensor 138, an example of at least one of electric sensors 38. As shown by FIG. 2, electric sensor 138 comprises low side electrodes 141, 143 and charged or active high side electrode 145. Active high side electrode 145 is sandwiched between low side electrodes 143. Low side electrodes 143 share active high side electrode 145, wherein an electrical field is formed between active electrode 145 and each of the two low side electrodes 141, 143. In one implementation, low side electrodes 141, 143 are each electrically grounded. In another implementation, low side electrodes 141, 143 comprise floating low side electrodes. As fluid flows across the electrodes 141, 143, 145 and through the electrical field, the particles or cells within the fluid impact the impedance of the electrical field. This impedance is sensed to identify characteristics of the cells or particles.

As further shown in FIG. 2, frequency source 62 is electrically coupled or connected to active electrode 145 to apply a controlled non-zero frequency of alternating current to active electrode 145. In one implementation, frequency source 62 is similarly connected to the active electrode 145 of each of electric sensors 38 of system 20, wherein frequency source 62 applies a different non-zero frequency of alternating current to the active electrode 145 of the different electric sensors. In other implementations, one or both of electric sensors 38 have a configuration or design different than the design of electric sensor 138 shown in FIG. 2.

Figure 3:
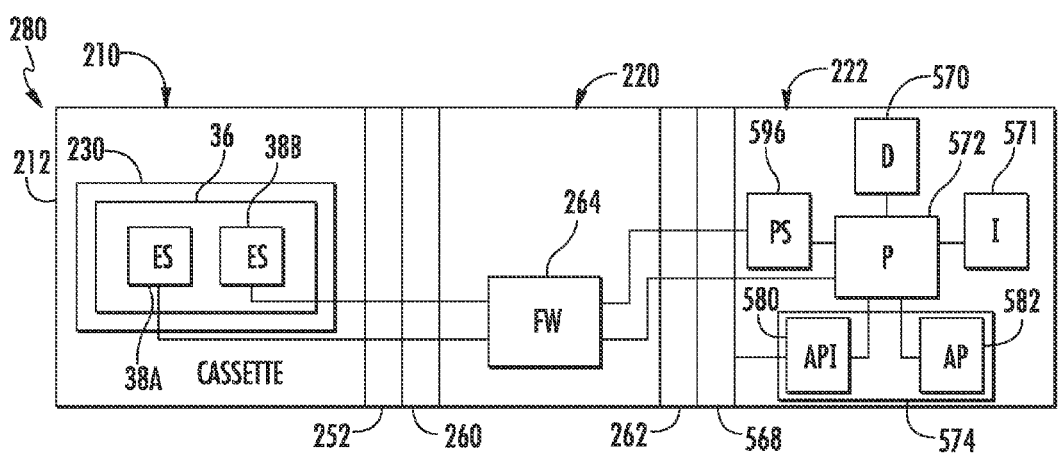
FIG. 3 is a schematic diagram of another example fluid testing system.

FIG. 3 schematically illustrates fluid testing system 200, an example implementation of fluid testing system 20. System 200 comprises cassette 210, cassette interface 220 and portable electronic device 222. Cassette 210 comprises a unit that is to be releasably connected to cassette interface 220. Cassette 210 comprises cassette body 212, microfluidic chip 230 and electrical connector 252.

Cassette body 212 supports microfluidic chip 230 and electrical connector 252. Microfluidic chip 230 comprises microfluidic channel 36 and electric sensors 38 described above. Electric sensors 38 are electrically connected to electrical connector 252.

Electrical connector 252 comprises a device by which microfluidic cassette 210 is releasably electrically connected to cassette interface 220. In one implementation, the electrical connection provided by electrical connector 252 facilitates transmission of electrical power for powering components of microfluidic chip 23, such as electric sensors 38. In one implementation, the electrical connection provided by electrical connector 252 facilitates transmission of electrical power in the form of electrical signals providing data transmission to microfluidic chip 230 to facilitate control of components of microfluidic chip 230, such as control of electric sensor 38. In one implementation, electrical connection provided by electrical connector 252 facilitates transmission of electrical power in the form electrical signals to facilitate the transmission of data from microfluidic chip 230 to the portable electronic device, such as the transmission of signals from sensors 38. In one implementation, electrical connector 252 facilitates each of the powering of microfluidic chip 230 as well as the transmission of data signals to and from microfluidic chip 230.

In the example illustrated, electrical connector 252 comprises a plurality of electrical contact pads which make contact with corresponding pads of cassette interface 220. In yet another implementation, electrical connector 252 comprises a plurality of electrical prongs or pins, a plurality of electrical pin or prong receptacles, or a combination of both. In the example illustrated, electrical connector 252 is electrically connected to components of microfluidic chip 130 via electrical traces formed within or upon cassette body 212 or formed upon or within a flexible circuit secured to cassette body 212.

Electrical connector 252 facilitates releasable electrical connection to a cassette interface 220 such that microfluidic cassette 210 may be separated from the cassette interface 220, facilitating disposal or storage of microfluidic cassette 210. As a result, microfluidic cassette 210, once used, may be exchanged with an unused microfluidic cassette 210; the unused microfluidic cassette 210 being connected to the cassette interface 220 and portable electronic device 222. Electrical connector 252 provides modularization, allowing the cassette interface 220 and the portable electronic device 222 along with their associated fluid analytical circuitry to be repeatedly reused while the cassette 210 is separated for storage or disposal.

Cassette interface 220, sometimes referred to as a "reader" or "dongle", interconnects and serves as an interface between microfluidic chip 230 of microfluidic cassette 210 and portable electronic device 222. Cassette interface 220 contains components or circuitry that is dedicated, customized or specifically adapted for controlling components of microfluidic cassette 210. Cassette interface 220 facilitates use of a general portable electronic device, loaded with the appropriate machine readable instruction and application program interface, but wherein the portable electronic device may omit the hardware or firmware specifically used to enable control of the components of cassette 210. As a result, cassette interface 220 facilitates use of multiple different portable electronic devices 222 which have simply been updated with an upload of machine readable instruction and an application program interface. Cassette interface 220 facilitates use of portable electronic device 222 that are not specifically designated or customized for use just with the particular microfluidic cassette 210.

At the same time, cassette interface 220 carries circuitry and electronic components dedicated or customized for the specific use of controlling the electronic components of cassette 210. Because cassette interface 220 carries much of the electronic circuitry and components specifically dedicated for controlling the electronic tones of cassette 210 rather than such electronic components being carried by cassette 210 itself, cassette 210 may be manufactured with fewer electronic components, allowing the costs, complexity and size of cassette 210 to be reduced. As a result, cassette 210 is more readily disposable after use due to its lower base cost. Likewise, because cassette interface 220 is releasably connected to cassette 210, cassette interface 220 is reusable with multiple exchanged cassettes 210. The electronic components carried by cassette interface 220 and dedicated or customized to the specific use of controlling the electronic components of a particular cassette 210 are reusable with each of the different cassettes 210 when performing fluid or blood tests on different fluid samples or fluid samples from different patients or sample donors.

In the example illustrated, cassette interface 220 comprises electrical connector 260, electrical connector 262 and controlling hardware, hardware comprising instructions, such as firmware 264. Electrical connector 260 comprises a device by which cassette interface 220 is releasably electrically connected directly to electrical connectors 252 of cassette 210. In one implementation, the electrical connection provided by electrical connector to 60 facilitates transmission of electrical power for powering electronic components of microfluidic chip 230, such as electric sensors 38 or a microfluidic pump (not shown). In one implementation, the electrical connection provided by electrical connector 260 facilitates transmission of electrical power in the form of electrical signals providing data transmission to microfluidic chip 230 to facilitate control of components of microfluidic chip 230. In one implementation, electrical connection provided by electrical connector 260 facilitates transmission of electrical power in the form electrical signals to facilitate the transmission of data from microfluidic chip 230 to the portable electronic device 222, such as the transmission of signals from sensor sensors 38. In one implementation, electrical connectors 260 facilitate each of the powering of microfluidic chip 230 as well as the transmission of data signals to and from microfluidic chip 230.

In the example illustrated, electrical connectors 260 comprise a plurality of electrical contact pads which make contact with corresponding pads of cassette 210. In yet another implementation, electrical connectors 260 comprise a plurality of electrical prongs or pins, a plurality of electrical pin or prong receptacles, or a combination of both. In one implementation, electrical connector 260 comprises a universal serial bus (USB) connector port to receive one end of a USB connector cord, wherein the other end of the USB connector cord is connected to cassette 210. In still other implementations, electrical connector 262 may be omitted, where cassette interface 220 comprises a wireless communication device, such as infrared, RF, Bluetooth other wireless technologies for wirelessly communicating between interface 220 and cassette 210.

Electrical connector 260 facilitates releasable electrical connection of cassette interface 220 to cassette 210 such that cassette interface to earn 20 may be separated from cassette 210, facilitating use of cassette interface 220 with multiple interchangeable cassettes 210 as well as disposal or storage of the microfluidic cassette 210 with the analyzed fluid, such as blood. Electrical connectors 260 facilitate modularization, allowing cassette interface 220 and associated circuitry to be repeatedly reused while cassette 210 is separated for storage or disposal.

Electrical connector 262 is similar to electrical connector 260 except that electrical connector 260 facilitates releasable connection of cassette interface 220 to portable electronic device 222. As a result, electrical connector 262 facilitates use of cassette interface 220 with multiple different portable electronic devices 222. In one implementation, electrical connector 262 comprises a plurality of distinct electrical contact pads which make contact with corresponding blood connectors of portable electronic device 222. In another implementation, electrical connector 262 comprises prongs or prong receiving receptacles. In one implementation, electrical connector 262 comprises a universal serial bus (USB) connector port to receive one end of a USB connector cord, or in the other end of the USB connector cord is connected to the portable electronic device 222. In still other implementations, electrical connector 262 may be omitted, where cassette interface 220 comprises a wireless communication device, utilizing infrared, RF, Bluetooth or other wireless technologies for wirelessly communicating between interface 220 and portable electronic device 222.

Firmware 264 comprises electronic componentry and circuitry or hardware carried by cassette interface 220 and specifically dedicated to the control of the electronic components and circuitry of microfluidic chip 230 and cassette 210. In the example illustrated, firmware 264 serves as part of a controller to control electric sensors 38.

Figure 4:
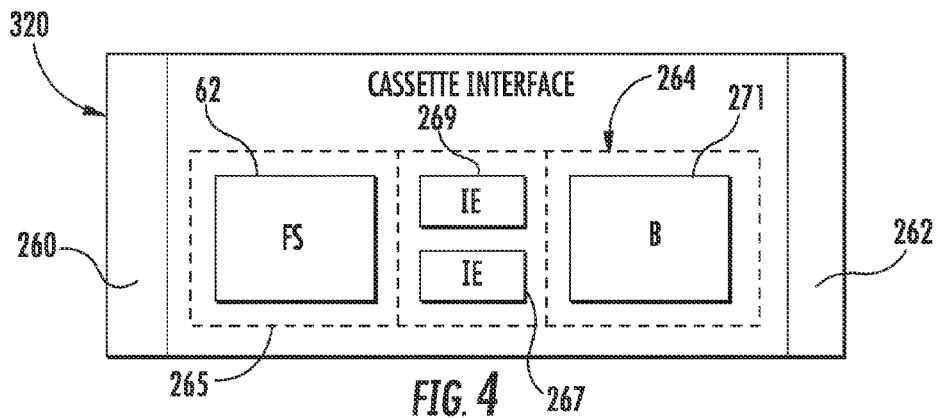
FIG. 4 is a schematic diagram of an example cassette interface of the fluid testing system of FIG. 3.

FIG. 4 schematically illustrates cassette interface 320, one example implementation of cassette interface 220. As shown by FIG. 4, cassette interface 320 comprises blood connectors 260, 262 and firmware 264. In the illustrated example, firmware 264 comprises at least one printed circuit board 265 which supports frequency source 62, a first impedance extractor 267 to receive first composite or base signals from electric sensor 38A and to extract first impedance signals from the first base signals, a second impedance extractor 269 to receive second composite or base signals from electric sensor 38B and to extract second impedance signals from the second base signals, and a buffer 271 to store the first and second impedance signals as or until the first second impedance signals are transmitted to portable electronic device 222. In one implementation, firmware 264 comprises a field programmable gate array which serves as a frequency source controller and the buffer 271. In another implementation, firmware 264 comprises an application-specific integrated circuit (ASIC) serving as a frequency source controller, the first impedance extractor 267, the second impedance extractor 269 and the buffer 271.

Figure 5:
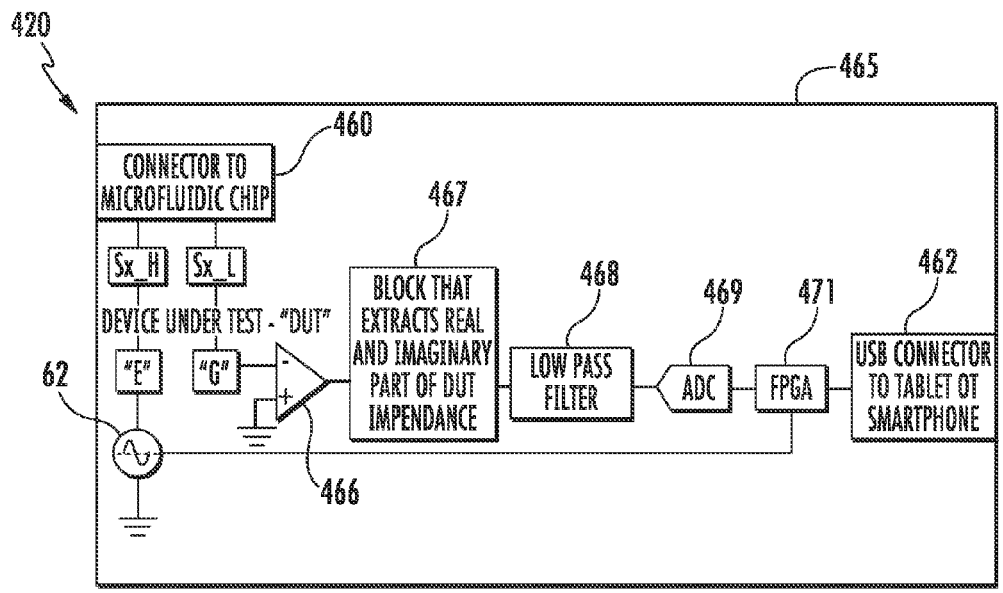
FIG. 5 is a schematic diagram of another example cassette interface.

FIG. 5 schematically illustrates cassette interface 420, another example implementation of cassette interface 220. Cassette interface 420 comprises electrical connectors 460, 462, printed circuit board 465, and firmware comprising frequency source 62, trans-impedance amplifier 466, impedance extractor 467, low pass filter 468, analog-to-digital converter 469, and field programmable gate array 471. In the example illustrated, electrical connector 460 comprises a series of electrical contacts that make electrical contact with corresponding electrical connectors 252 of cassette 210. Electrical connector 460 transmits electrical signals to and from each of the sensors 38 of cassette 210. As schematically represented in FIG. 5, electrical connector 460 electrically connects frequency source 62 (described above) to the active high side electrodes "E" (electrodes 145 in FIG. 2) on microfluidic chip 230 via a corresponding sensor pad (Sx_H, wherein x denotes the sensor pad number on cassette 210) on cassette 210. Electrical connector 460 further electrically connects each of the low side electrodes "G" (electrodes 141, 143 in FIG. 2) on microfluidic chip 232 trans-impedance amplifier 466 via a corresponding sensor pad (Sx_L, wherein x denotes a sensor pad number on cassette 210) on cassette 210. Amplifier 466 is formed on per circuit board 465 and amplifies the base or composite signal and transmits the amplified signal to impedance extractor 467.

Impedance extractor 467 comprises circuitry to extract, from the composite or base analog signal received from amplifier 466, the real and imaginary parts of the device under test impedance. In one implementation, extractor 467 comprises mixers and amplifiers and other circuitry to perform analog quadrature amplitude modulation (QAM) which utilizes radiofrequency (RF) components to extract the frequency component out so that the actual shift in phase caused by impedance of the device under test (the particular sensor 38) may be utilized. The extracted impedance signals are then passed through low pass filter 468 and converted into digital signals by analog-to-digital converter 469.

Field programmable gate array 471 processes and stores the digital impedance signal received from converter 469 so as to buffer such signals or data prior to being transmitted to portable electronic device 222. In the example illustrated, field programmable gate array 471 further serves as a frequency source controller or driver for frequency source 62, controlling the output of different frequencies of alternating current to electric sensors 38. In yet other implementations, field programmable gate array 471 serves as a driver for other electronic components on micro-fluidic chip 230 such as microfluidic pumps (such as resistors) and other electronic components upon chip 230.

In another implementation, extractor 467, filter 468, analog-to-digital converter 469 and field programmable gate array 471 may be omitted and replaced with another form of a microcontroller such as an application-specific integrated circuit (ASIC) which performs similar functions. In such an implementation, an analog-to-digital converter is interposed between amplifier 466 and the ASIC. Because printed circuit board 465 carries each of the electronic components or circuitry forming the firmware that interact between the application programming interface of portable electronic device 222 and microfluidic chip 230 of cassette 210, system 200 carries out testing of fluid samples using electric sensors 38 in a very portable and compact fashion as compared to benchtop testing systems.

Portable electronic device 222 comprises a mobile electronic device to receive data from microfluidic chip 230. Portable electronic device 222 is releasably or removably connected to chip 430 indirectly via cassette interface 220. Portable electronic device 222 performs varies functions using data received from chip 430. For example, in one implementation, portable electronic device 222 stores the data. In another implementation, portable electronic device 222 additionally or alternatively manipulates a processes the data. In yet another implementation, portable electronic device 222 additionally or alternatively displays the data and/or further transmits the data across a local area network or wide area network to a server providing additional storage and/or processing capabilities.

In the example illustrated, portable electronic device 222 comprises electrical connectors 568, power source 569, display 570, input 571, processor 572, and memory 574. Electrical connectors 568 are similar to electrical connectors 262. In one implementation, electrical connector 568 comprises a plurality of distinct electrical contact pads which make contact with corresponding blood connectors of cassette interface 220. In another implementation, electrical connector to 62 comprises prongs or prong receiving receptacles. In one implementation, electrical connector 568 comprises a universal serial bus (USB) connector port to receive one end of a USB connector cord, wherein the other end of the USB connector cord is connected to cassette interface 220. In still other implementations, electrical connector 568 may be omitted, where the portable electronic device 222 comprises a wireless communication device, utilizing infrared, RF, Bluetooth or other wireless technologies for wirelessly communicating between interface 220 and portable electronic device 222.

Power source 569 comprise a source of electrical power carried by portable electronic device 222 for supplying power to cassette interface 220 and cassette 210. Power source 569 comprises various power control electronic componentry which control characteristics of the power (voltage, current) being supplied to the various electronic components of cassette interface 220 and cassette 210. Because power for both cassette interface to earn 20 and cassette 210 are supplied by portable electronic device to 22, the size, cost and complexity of cassette interface 220 and cassette 210 are reduced. In other implementations, power for cassette 210 and is interface 220 are supplied by a battery located on cassette interface 220. In yet another implementation, power for cassette 210 is provided by a battery carried by cassette 210 and power for interface to earn 20 supplied by a separate dedicated battery for cassette interface 220.

Display 570 comprises a monitor or screen by which data is visually presented. In one implementation, display 570 facilitates a presentation of graphical plots based upon data received from chip 230. In some implementations, display 570 may be omitted or may be replaced with other data communication elements such as light emitting diodes, auditory devices are or other elements that indicate results based upon signals or data received from chip 230.

Input 571 comprises a user interface by which a person may input commands, selection or data to portable electronic device 222. Examples of input 571 include, but are not limited to, a keyboard, a touchscreen (in one implementation a touchscreen of display 570), a touchpad, a mouse, a microphone with associated speech recognition programs and the like. In one implementation come input 571 facilitates input of different frequencies of alternating current corresponding to different tests to be run upon a fluid sample placed in cassette 210.

Processor 572 comprises at least one processing unit designed to generate control signals controlling the operation of sensors 338 as well as the acquisition of data from sensors 338. In the example illustrated, processor 572 further analyzes data received from chip 230 to generate output that is stored in memory 574, displayed on display 570 and/or further transmitted across a network.

Memory 574 comprises a non-transitory computer-readable medium containing instructions for directing the operation of processor 572. As schematically shown by FIG. 3, memory 574 comprises or stores an application programming interface 580 and an overarching application program. Application programming interface 580 comprises a library of routines, protocols and tools, which serve as building blocks, for carrying out various functions or tests using cassette 210. Application programming interface 580 comprises programmed logic that accesses the library and assembles the "building blocks" or modules to perform a selected one of various functions or tests using cassette 210. For example, in one implementation, application programming interface 582 comprises an application programming interface library that contains routines for directing the firmware 264 to place electric sensors 38 in selected operational states, such as through the application of different frequencies of alternating current. In one implementation, the library also contains routines for directing firmware 264 to operate fluid pumps or dynamically adjusts operation of such pumps or electric sensors 38 in response to a sensed temperature of the fluid being tested. In one implementation, portable electronic device 222 comprises a plurality of application programming interfaces 582, each application programming interface 582 being specifically designed are dedicated to a particular overall test. For example, one application programming interface 582 may be directed to performing cytology tests. Another application program interface 582 may be directed to performing coagulation tests. In such implementations, the multiple application programming interfaces 582 may share the library of routines, protocols and tools.

Application programming interface 582 facilitates testing of fluids using cassette 210 under the direction of different application programs. In other words, application programming interface 582 provides a universal programming or set of commands for firmware 264 that may be used by any of a variety of different application programs. For example, a user of portable electronic device 222 is able to download or install any of a number of different application programs, wherein each of the different application programs is designed to utilize the application program interface 582 so as to carry out tests using cassette 210. As noted above, firmware 264 interfaces between application programming interface 582 and the actual hardware or electronic componentry found on the cassette 210 and, in particular, microfluidic chip 230.

Application program 580 comprises an overarching program contained in memory 574 that facilitates user interaction with application programming interface 582 or the multiple application programming interfaces 582 stored in memory 574. Application program 580 presents output on display 570 and receives input through input 571. Application program 580 communicates with application program interface 582 in response to input received through input 571. For example, in one implementation, a particular application program 580 presents graphical user interfaces on display 570 prompting a user to select which of a variety of different testing options are to be run using cassette 210. Based upon the selection, application program 580 interacts with a selected one of the application programming interfaces 582 to direct firmware 264 to carry out the selected testing operation using the electronic componentry of cassette 210. Sensed values received from cassette 210 using the selected testing operation are received by firmware 264 and are processed by the selected application program interface 582. The output of the application programming interface 582 is generic data, data that is formatted so as to be usable by any of a variety of different application programs. Application program 580 presents the base generic data and/or performs additional manipulation or processing of the base data to present final output to the user on display 570.

Although application programming interface 582 is illustrated as being stored in memory 574 along with the application program 580, in some implementations, application programming interface 582 is stored on a remote server or a remote computing device, wherein the application program 580 on the portable electronic device 222 accesses the remote application programming interface 582 across a local area network or a wide area network. In some implementations, application programming interface 582 is stored locally on memory 574 while application program 580 is remotely stored and accessed across a local area network or wide area network. In still other implementations, both application programming interface 582 and application program 580 are contained on a remote server or remote computing device and accessed across a local area network or wide area network (sometimes referred to as cloud computing).

In one implementation, portable electronic device 432 comprises a tablet computer. In other implementations, portable electronic device 432 comprises a smart phone or laptop or notebook computer. In yet other implementations, portable electronic device 432 is replaced with a stationary computing device, such as a desktop computer or all-in-one computer.

Figure 6:
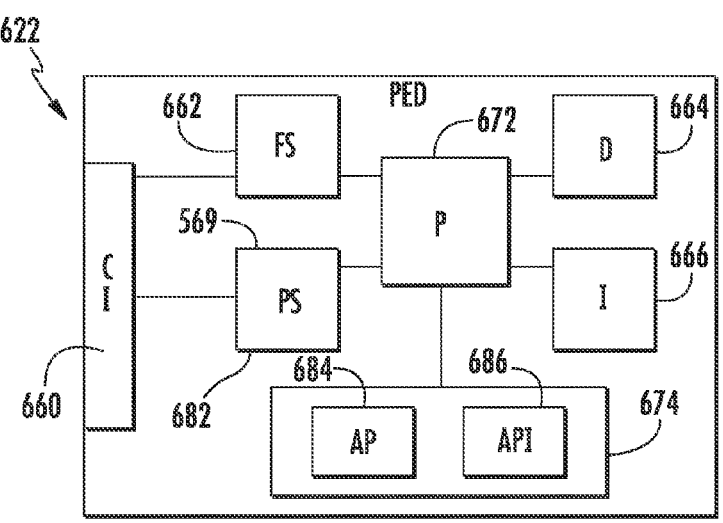
FIG. 6 is a schematic diagram of an example portable electronic device for use as part of a fluid testing system.

FIG. 6 schematically illustrates portable electronic device 622, another example implementation of portable electronic device 222. Portable electronic device 622 is specifically designated for use in fluid testing using cassette 210. In the example illustrated, portable electronic device 622 comprises electronics and firmware, that might otherwise be found on cassette interface 220, that facilitate direct control of and communication with cassette 210 by portable electronic device 222. Because portable electronic device 622 is not generic, but is specifically designed to work with cassette 210, portable electronic device 622 is to directly connect to cassette 210 without any intervening cassette interface 220. In one implementation, portable electronic device 622 comprises a port which receives cassette 210. In another implementation, portable electronic device 622 comprise a plug to be inserted into a corresponding port in cassette 210. In yet another implementation, electronic device 622 includes a port for direct connection to a cassette by an intermediate cord or cable. In still another implementation, portable electronic device 222 incorporates a transmitter to wirelessly communicate with cassette 210.

Portable electronic device 622 comprises communication interface 660, frequency source 662, user interface elements comprising display 664 and input 666, power supply 669, processor 672 and memory 674. Communication interface 660 comprise a device by which portable electronic device 622 directly communicate with microfluidic chip 230 on cassette 210 (shown in FIG. 3). In one implementation, communication interface 660 comprises a plurality of distinct electrical contact pads which make contact with corresponding electrical connectors of cassette interface 220. In another implementation, communication interface 660 comprises prongs or prong receiving receptacles. In one implementation, communication interface 660 comprises a universal serial bus (USB) connector port to receive one end of a USB connector cord, wherein the other end of the USB connector cord is connected to cassette interface 220. In still other implementations, communication interface 660 comprises a wireless communication device, utilizing infrared, RF, Bluetooth or other wireless technologies for wirelessly communicating between cassette 210 and portable electronic device 622.

Display 664 comprises a monitor or screen by which data is visually presented. In one implementation, display 664 facilitates a presentation of graphical plots based upon data received from chip 230. In some implementations, display 664 may be omitted or may be replaced with other data communication elements such as light emitting diodes, auditory devices are or other elements that indicate results based upon signals or data received from chip 230.

Input 666 comprises a user interface by which a person may input commands, selection or data to portable electronic device 622. Examples of input 666 include, but are not limited to, a keyboard, a touchscreen (in one implementation a touchscreen of display 664), a touchpad, a mouse, a microphone with associated speech recognition program and the like. In one implementation, input 666 facilitates input of different frequencies of alternating current corresponding to different tests to be run upon a fluid sample placed in cassette 210.

Power supply 669 is similar to power supply 569 described above except the power supply 669 supplies electrical power to the electronic power consuming componentry of cassette 210.

Processor 672 comprises at least one processing unit designed to generate control signals controlling the operation of sensors 338 as well as the acquisition of data from sensors 338. In the example illustrated, processor six escape further analyzes data received from chip 230 to generate output that is stored in memory 674, displayed on display 664 and/or further transmitted across a network.

Memory 674 comprises a non-transitory computer-readable medium containing instructions for directing the operation of processor 672. As schematically shown by FIG. 6, memory 674 comprises or stores application programming interface 680 and application program 582 (described above). Application programming interface 680 is similar to application programming interface 580 described above except that application programming interface 680 includes in its library routines, protocols and tools for carrying out the functions previously described as being carried out by firmware 264. Application programming interface 680 utilizes the processing power of processor 672 to carry out the functions previously carried out by the field programmable gate array 471 or the corresponding ASIC of cassette interface 220. In particular, portable electronic device 622 comprises electronic componentry (such as amplifiers, analog-to-digital converters and the like) while application programming interface 680 includes in its libraries routines, protocols and tools for extracting impedance signals from the composite or base signals, buffering the impedance signals or data and outputting control signals to control the application of different frequencies of alternating current to electric sensors 38 by frequency source 662. In some implementations, the application programming interface library additionally includes routines for controlling pumps and monitoring and controlling temperature sensors which are provided on microfluidic chip 230 of cassette 210. The additional routines for carrying out functions previously performed by firmware 264 are automatically invoked during the operation of system 200 in response to a particular fluid test or a particular mode of a fluid test being selected by the user using application program 582.

In some implementations, portable electronic device 622 (or portable electronic device 222 described above) comprises multiple application programming interfaces 686, wherein a particular cassette 210 may not be able to carry out each of the testing modes or tests provided by the application programming interfaces 686. In such an implementation, the portable electronic device 622, 222 carries out a cross check with the particular cassette 210 to identify the capabilities of the particular cassette 210 connected to the portable electronic device 622, 222 at the particular time. If the user selects a particular testing mode or test through the application program 582 that is not available with the current set to earn 10 that is connected to the portable electronic device 622, 222, this incompatibility is communicated to the user on display 570.

In one implementation, portable electronic device 622 comprises a tablet computer. In other implementations, portable electronic device 622 comprises a smart phone or laptop or notebook computer. In yet other implementations, portable electronic device 622 is replaced with a stationary computing device, such as a desktop computer or all-in-one computer.

Figure 7:
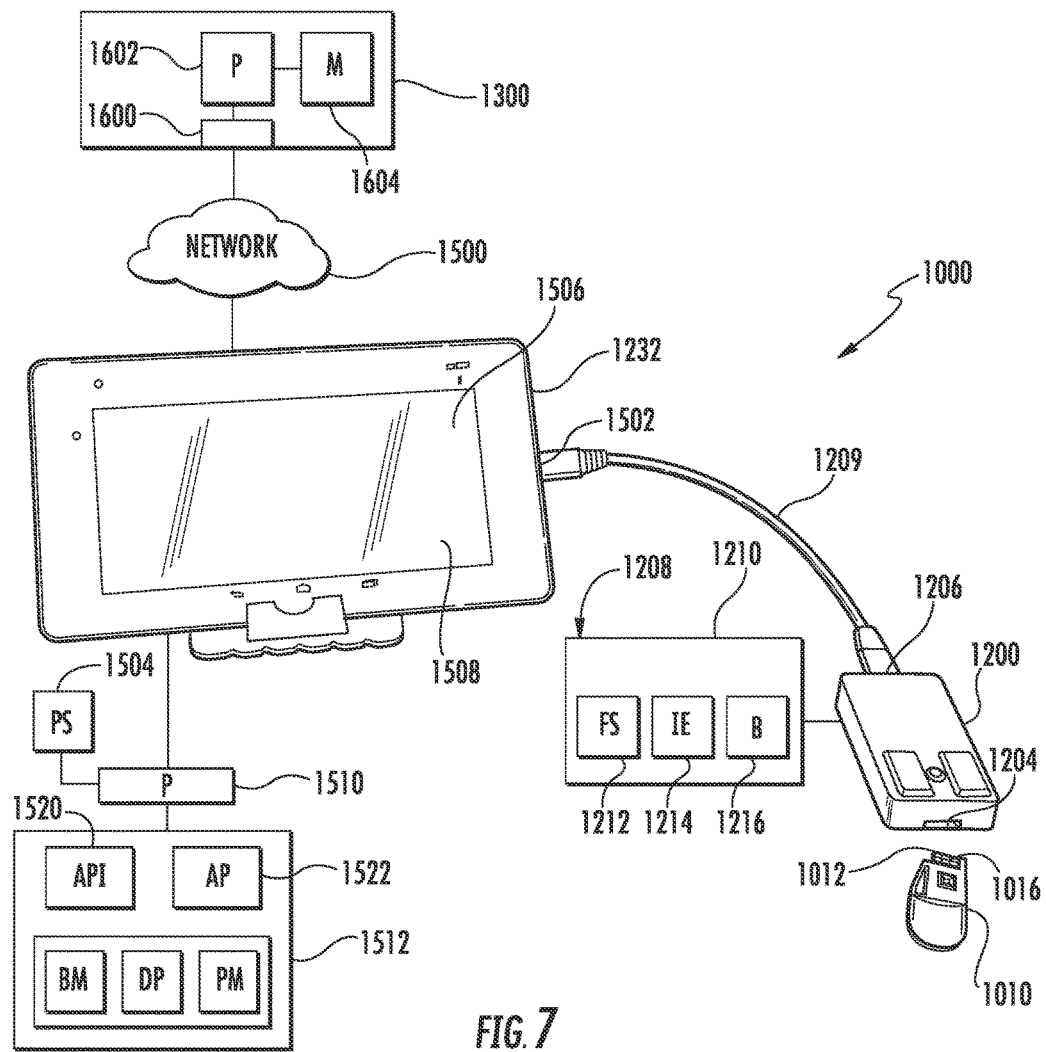
FIG. 7 is a schematic diagram of another example fluid testing system.

FIG. 7 illustrates an example microfluidic diagnostic or testing system 1000. System 1000 comprises a portable electronic device driven, impedance-based system by which samples of fluid, such as blood samples, are analyzed. For purposes of this disclosure, the term "fluid" comprises the analyte in or carried by the fluid such as a cell, particle or other biological substance. The impedance of the fluid refers to the impedance of the fluid and/or any analyte in the fluid. System 1000, portions of which are schematically illustrated, comprises microfluidic cassette 1010, cassette interface 1200, mobile analyzer 1232 and remote analyzer 1300.

Overall, microfluidic cassette 1010 receives a fluid sample and outputs signals based upon sensed characteristics of the fluid sample. Interface 1200 serves as an intermediary between mobile analyzer 1232 and cassette 1010. Interface 1200 removably connects to cassette 1010 and facilitates transmission of electrical power from mobile analyzer 1232 to cassette 1010 to operate pumps and sensors on cassette 1010. Interface 1200 further facilitates control of the pumps and sensors on cassette 1010 by mobile analyzer 1232. Mobile analyzer 1232 controls the operation cassette 1010 through interface 1200 and receive data produced by cassette 1010 pertaining to the fluid sample being tested. Mobile analyzer 1232 analyzes data and produces output. Mobile analyzer 1232 further transmits processed data to remote analyzer 1300 for further more detailed analysis and processing. System 1000 provides a portable diagnostic platform for testing fluid samples, such as blood samples.

Figure 10A:
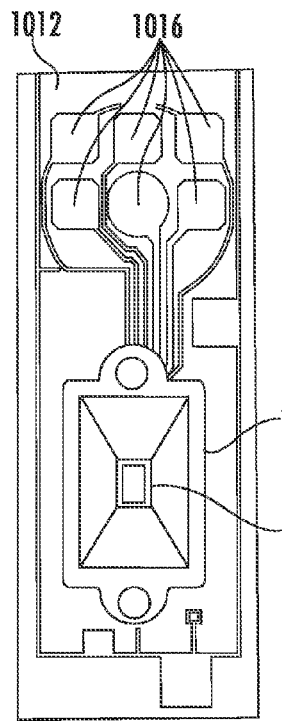
FIG. 10A is a top view of an example cassette board supporting an example microfluidic cassette and funnel.
Figure 10B:
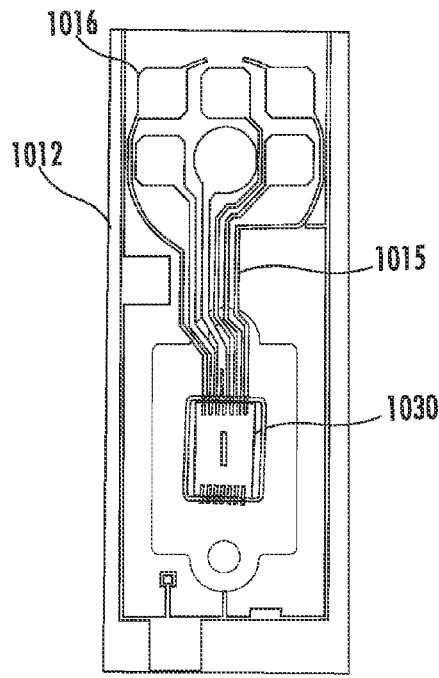
FIG. 10B is a bottom view of the cassette board of FIG. 10A.

FIGS. 8-21 illustrate microfluidic cassette 1010 in detail. As shown by FIGS. 8-10, cassette 1010 comprises cassette board 1012, cassette body 1014, membrane 1015 and microfluidic chip 1030. Cassette board 1012, shown in FIGS. 10A and 10B, comprises a panel or platform in which or upon which fluid chip 1030 is mounted. Cassette board 1012 comprises electrically conductive lines or traces 1015 which extend from electrical connectors of the microfluidic chip 1030 to electrical connectors 1016 on an end portion of cassette board 1012. As shown in FIG. 8, electrical connectors 1016 are exposed on an exterior cassette body 1014. As shown by FIG. 7, the exposed electrical connectors 1016 are to be inserted into interface 1200 so as to be positioned in electrical contact with corresponding electrical connectors within interface 1200, providing electrical connection between microfluidic chip 1030 and cassette interface 1200.

Cassette body 1014 partially surrounds cassette board 1012 so as to cover and protect cassette board 1012 and microfluidic chip 1030. Cassette body 1014 facilitates manual manipulation of cassette 1010, facilitating manual positioning of cassette 1010 into releasable interconnection with interface 1200. Cassette body 1014 additionally positions and seals against a person's finger during the acquisition of a fluid or blood sample while directing the received fluid sample to microfluidic chip 1030.

In the example illustrated, cassette body 1014 comprises finger grip portion 1017, sample receiving port 1018, residence passage 1020, sample holding chamber 1021, chip funnel 1022, vent 1023 and discharge reservoir 1024. Finger grip portion 1017 comprises a thin portion of body 1014 opposite to the end of cassette 1010 at which electrical connectors 1016 are located. Finger grip portion 1017 facilitates gripping of cassette 1010 in connection or insertion of cassette 1010 into a receiving port 1204 of cassette interface 1200 (shown in FIG. 7). In the example illustrated, finger grip portion 1017 has a width W of less than or equal to 2 inches, a length L of less than or equal to 2 inches and a thickness of less than or equal to 0.5 inches.

Sample receiving port 1018 comprises an opening into which a fluid sample, such as a blood sample, is to be received. In the example illustrated, sample receiving port 1018 has a mouth 1025 that is formed on a top surface 1027 of an elevated platform or mound 1026 that extends between finger grip portion 1017 and the exposed portion of cassette board 1012. Mound 1026 clearly identifies the location of sample receiving port 1018 for the intuitive use of cassette 1010. In one implementation, the top surface 1027 is curved or concave to match or approximately match the lower concave surface of a finger of a person so as to form an enhanced seal against the bottom of the person's finger from which the sample is taken. Capillary action pulls in blood from the finger which forms the sample. In one implementation, the blood sample is of 5 to 10 microliters. In other implementations, port 1018 is located at alternative locations or mound 1026 is omitted, for example, as depicted in FIG. 9A. Although FIG. 9A illustrates cassette 1010 having a slightly different outer configuration for cassette body 1014 as compared to body 1014 shown in FIG. 8, wherein the cassette body 1014 shown in FIG. 9A omits mound 1026, those remaining elements or components shown in FIGS. 8 and 9A are found in both of the cassette bodies shown in FIGS. 8 and 9A.

As shown by FIGS. 9A-9C, residence passage 1020 comprises a fluid channel, conduit, tube or other passage extending between sample input port 1018 and sample holding chamber 1021. Residence passage 1020 extends between sample input port 1018 and sample holding chamber 1021 in a tortuous fashion, an indirect or non-linear fashion full of twists and turns, to lengthen the time for a received sample, input through sample input port 1018, to travel or flow to chip 1030. Residence passage 1018 provides a volume in which the fluid sample being tested and a fluid reagent may mix prior to reaching chip 1030. In the example illustrated, residence passage 263 is circuitous, comprising a circular or helical passage winding in the space of cassette body 1012 between port 1018 and chip 1030. In another implementation, residence passage thousand 20 twists and turns, zigzags, snakes, serpentines and/or meanders in a zigzag fashion within the space between sample input port 1018 and chip 1030.

In the example illustrated, residence passage 1020 extends in a downward direction towards microfluidic chip 1030 (in the direction of gravity) and subsequently extends in an upward direction away from microfluidic chip 1030 (in a direction opposite to that of gravity). For example, as shown by FIGS. 9A and 9B, upstream portions 1028 extend vertically below the downstream end portion 1029 of residence passage 1020 that is adjacent to and directly connected to sample holding chamber 1021. Although upstream portions receive fluid from input port 1018 before end portion 1029, end portion 1029 is physically closer to input port 1018 in a vertical direction. As a result, fluid flowing from the upstream portions flows against gravity to the downstream or end portion 1029. As described hereafter, in some implementations, residence passage 1020 contains a reagent 1025 which reacts with the fluid sample or blood sample being tested. In some circumstances, this reaction will produce residue or fallout. For example, a fluid sample such as blood that has undergone lysis will have lysed cells or lysate. Because end portion 1029 of residence passage 1020 extends above upstream portions 1028 of residence passage 1020, such residue or fallout resulting from the reaction of the fluid sample with reagent 1025 settles out and is trapped or retained within such upstream portions 1028. In other words, the amount of such residue or fallout passing through residence passage 1020 to microfluidic chip 1030 is reduced. In other implementations, residence passage 1020 extends in a downward direction to sample holding chamber 1021 throughout its entire course.

Sample holding chamber 1021 comprises a chamber or internal volume in which the fluid sample or blood sample being tested collects above chip 1030. Chip funnel 1022 comprises a funneling device that narrows down to chip 1030 so as to funnel the larger area of chamber 1021 to the smaller fluid receiving area of chip 1030. In the example illustrated, sample input port 1018, residence passage 1020, sample holding chamber 1021 and chip funnel 1022 form an internal fluid preparation zone in which a fluid or blood sample may be mixed with a reagent before entering chip 1030. In one implementation, the fluid preparation zone has a total volume of 20 to 250 μL. In other implementations, the fluid preparation zone provided by such internal cavities may have other volumes.

As indicated by stippling in FIG. 9A, in one implementation, cassette 1010 is prefilled with a fluid reagent 1025 prior to insertion of a sample fluid to be tested into port 1018. Fluid reagent 1025 comprises a composition that interacts with the fluid to be tested, enhancing the ability of microfluidic chip 130 to analyze a selected characteristic or a group of selected characteristics of the fluid to be tested. In one implementation, fluid reagent 1025 comprises a composition to dilute the fluid being tested. In one implementation, fluid reagent 1025 comprises a composition to perform lysis on the fluid or blood being tested. In yet another implementation, fluid reagent 264 comprises a composition to facilitate tagging of selected portions of the fluid being tested. For example, in one implementation, fluid reagent 1025 comprises magnetic beads, gold beads or latex beads. In other implementations, fluid reagent 1025 comprises other liquid or solid compositions or liquids, distinct from the sample fluid to be tested, that interact with or that modify the sample fluid placed within sample input port 1018 prior to the sample fluid being received, processed and analyzed by microfluidic chip 1030.

Vents 1023 comprise passages communicating between sample holding chamber 1021 and the exterior of cassette body 1014. In the example illustrated in FIG. 8, vents 1023 extend through the side of mount 1026. Vents 1023 are sized small enough to retain fluid within sample holding chamber 1021 through capillary action but large enough so as to permit air within holding chamber 1021 to escape as holding chamber 1021 is filled with fluid. In one implementation, each of their vents has an opening or diameter of 50 to 200 micrometers.

Discharge reservoir 1024 comprises a cavity or chamber within body 1014 arranged to receive fluid discharged from chip 1030. Discharge reservoir 1024 is to contain fluid that has been passed through chip 1030 and that has been processed or tested. Discharge reservoir 1024 receives processed or tested fluid such that the same fluid is not tested multiple times. In the example illustrated, discharge reservoir 1024 is formed in body 1014 below chip 1030 or on a side of chip 1030 opposite to that of chip funnel 1022 and sample holding chamber 1021 such that chip 1030 is sandwiched between chip funnel 1022 and discharge reservoir 1024. In one implementation, discharge reservoir 1024 is completely contained within body 1014 and is inaccessible (but through the destruction of body 1014 such as by cutting, drilling or other permanent destruction or breaking of body 1014), locking the processed or tested fluid within body 112 for storage or subsequent sanitary disposal along with disposal of cassette 1010. In yet another implementation, discharge reservoir 1024 is accessible through a door or septum, allowing processed or tested fluid to be withdrawn from reservoir 1020 for further analysis of the tested fluid, for storage of the tested fluid in a separate container or for emptying of reservoir 1024 to facilitate continued use of cassette 1010.

In some implementations, microfluidic reservoir 1024 is omitted. In such implementations, those portions of the fluid samples or blood samples that have been tested are processed by microfluidic chip 1030 are recirculated back to an input side or input portion of microfluidic chip 1030. For example, in one implementation, microfluidic chip 1030 comprises a microfluidic reservoir which receives fluid through chip funnel 1022 on a input side of the sensor or sensors provided by microfluidic chip 1030. Those portions of a fluid sample or blood sample that have been tested are returned back to the microfluidic reservoir on the input side of the sensor or sensors of microfluidic chip 1030.

Membrane 1015 comprises an imperforate, liquid impermeable panel, film or other layer of material adhesively are otherwise secured in place so as to extend completely across and completely cover mouth 1025 of port 1018. In one implementation, membrane 1015 serves as a tamper indicator identifying if the interior volume of cassette 1010 and its intended contents have been compromised or tampered with. In implementations where the sample preparation zone of cassette 1010 has been prefilled with a reagent, such as reagent 1025 described above, membrane 1015 seals the fluid reagent 1025 within the fluid preparation zone, within port 1018, residence passage 1020, fluid holding chamber 1021 and chip funnel 1022. In some implementations, membrane 1015 additionally extends across vents 1023. Some implementations, membrane 1015 is additionally gas or air impermeable.

In the example illustrated, membrane 1015 seals or contains fluid reagent 1025 within cassette 1010 at least until the fluid sample is to be deposited into sample input port 1018. At such time, membrane 1015 may be peeled away, torn or punctured to permit insertion of the fluid sample through mouth 1018. In other implementations, membrane 1015 may comprises septum through which a needle is inserted to deposit a fluid or blood sample through mouth 1018. Membrane 1015 facilitates pre-packaging of fluid reagent 1025 as part of cassette 1010, wherein the fluid agent 1025 is ready for use with the subsequent deposits of the fluid sample to be tested. For example, a first cassette 1010 containing a first fluid reagent 1025 may be predesigned for testing a first characteristic of a first sample of fluid while a second cassette 1010 containing a second fluid reagent 1025, different than the first fluid reagent 1025, may be predesigned for testing a second characteristic of a second sample of fluid. In other words, different cassettes 1010 may be specifically designed for testing different characteristics depending upon the type or a quantity of fluid reagent 1025 contained therein.

Figure 11:
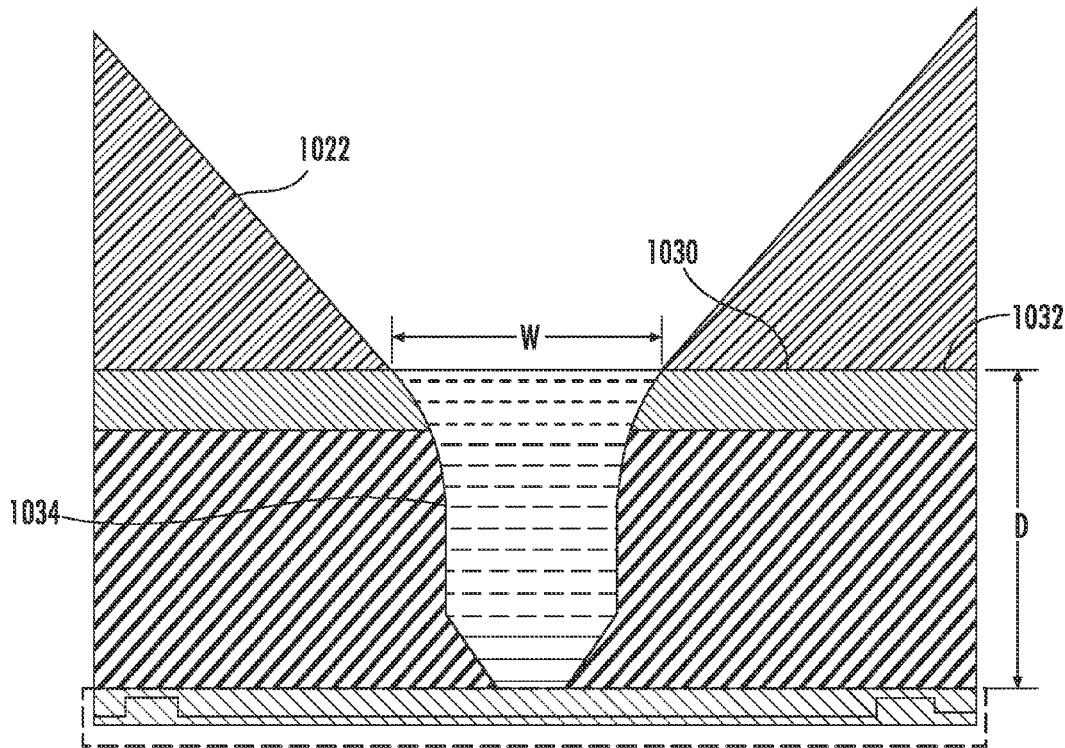
FIG. 11 is a fragmentary sectional view of a portion of the cassette board of FIG. 10A.

FIGS. 10A, 10B and 11 illustrate microfluidic chip 1030. FIG. 10A illustrates a top side of cassette board 1012, chip funnel 1022 and microfluidic chip 1030. FIG. 10A illustrates microfluidic chip 1030 sandwiched between chip funnel 1022 and cassette board 1012. FIG. 10B illustrate a bottom side of the set board 1012 and microfluidic chip 1030. FIG. 11 is a cross-sectional view of microfluidic chip 1030 below chip funnel 1022. As shown by FIG. 11, microfluidic chip 1030 comprises a substrate 1032 formed from a material such as silicon. Microfluidic chip 1030 comprises a microfluidic reservoir 1034 formed in substrate 1032 and which extends below chip funnel 1022 to receive the fluid sample (with a reagent in some tests) into chip 1030. In the example illustrated, microfluidic reservoir has a mouth or top opening having a width W of less than 1 mm and nominally 0.5 mm. Reservoir 1030 has a depth D of between 0.5 mm and 1 mm and nominally 0.7 mm. As will be described hereafter, microfluidic chip 1030 comprises pumps and sensors along a bottom portion of chip 1030 in region 1033.

Figure 12:
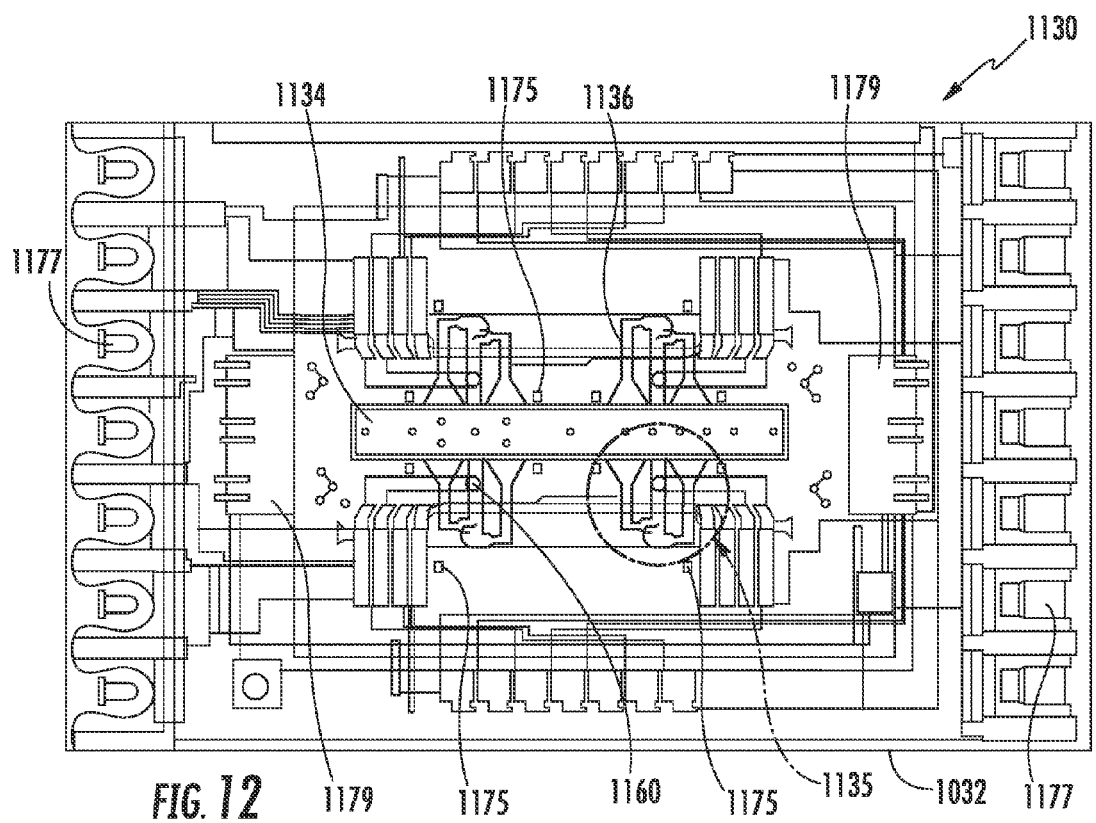
FIG. 12 is a top view of another example of the microfluidic chip of the cassette of FIGS. 8 and 9A.
Figure 13:
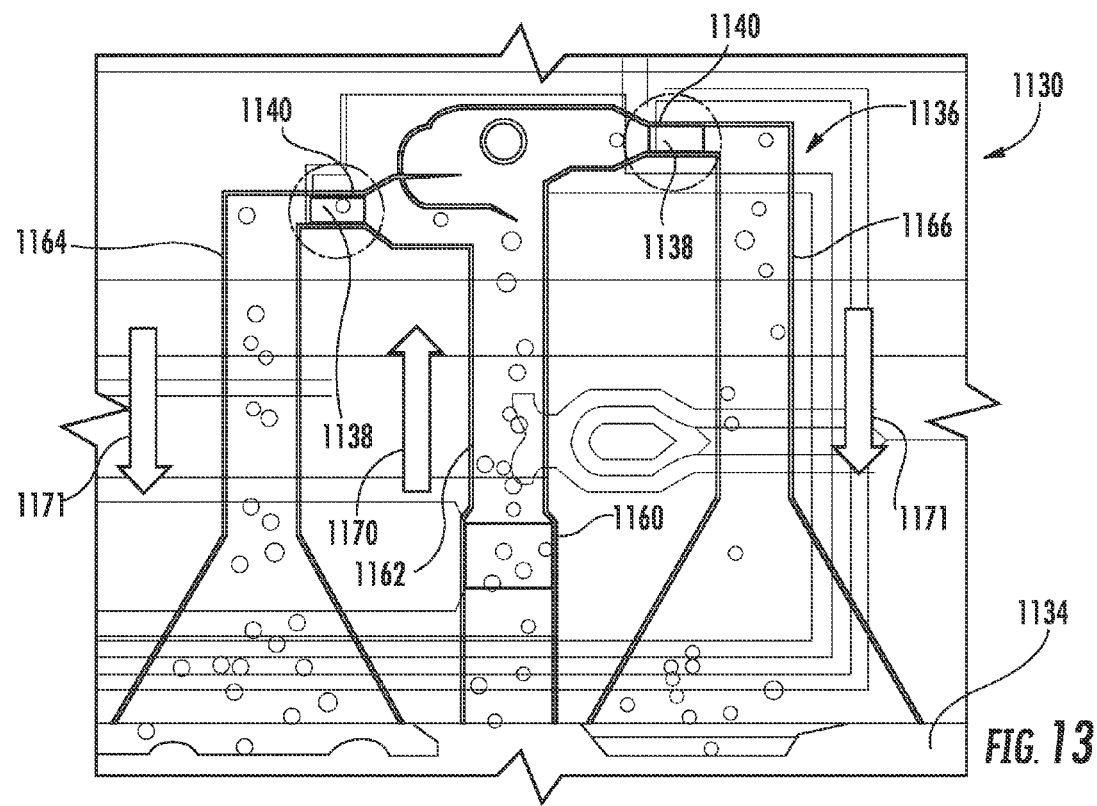
FIG. 13 is an enlarged fragmentary top view of an example sensing region of the microfluidic chip of FIG. 12.

FIGS. 12 and 13 are enlarged views of microfluidic chip 1130, an example implementation of microfluidic chip 1030. Microfluidic chip 1130 integrates each of the functions of fluid pumping, impedance sensing and temperature sensing on a low-power platform. Microfluidic chip 1130 is specifically designed for use with a cassette 1010 having a cassette body 1014 that omits discharge reservoir 1024. As will be described hereafter, microfluidic chip 1133 recirculates portions of a fluid sample, that has been tested, back to an input or upstream side of the sensors of microfluidic chip 1133. As shown by FIG. 12, microfluidic chip 1030 comprises substrate 1032 in which is formed microfluidic reservoir 1034 (described above). In addition, microfluidic chip 1130 comprises multiple sensing regions 735, each sensing region comprising a microfluidic channel 1136, micro-fabricated integrated sensors 1138, and a pump 1160.

FIG. 13 is an enlarged view illustrating one of sensing regions 1135 of chip 1130 shown in FIG. 12. As shown by FIG. 13, microfluidic channel 1136 comprises a passage extending within or formed within substrate 1032 for the flow of a fluid sample. Channel 1136 comprises a pump containing central portion 1162 and a pair of sensor containing branch portions 1164, 1166. Each of branch portions 1164, 1166 comprises a funnel-shaped mouth that widens towards microfluidic reservoir 1134. Central portion 1162 extends from reservoir 1134 with a narrower mouth opening to reservoir 1134. Central portion 1162 contains pump 1160.

Sensor containing branch portions 1164, 1166 stem or branch off of opposite sides of central portion 162 and extend back to reservoir 1134. Each of branch portions 1164, 1166 comprises a narrowing portion, throat or constriction 1140 through with the fluid flows. For purposes of this disclosure, a "constriction" means any narrowing in at least one dimension. A "constriction" may be formed by (A) one side of a channel having a protruberance projecting towards the other side of the channel, (B) both sides of a channel having at least one protruberance projecting towards the other side of the channel, wherein such multiple protruberances are either aligned with one another or are staggered along the channel or (C) at least one column or pillar projecting between two walls of the channel to discriminate against what can or cannot flow through the channel.

In one implementation, branch portions 1164, 1166 are similar to one another. In another implementation, branch portions 1164, 1166 are shaped or dimensioned different from one another so as to facilitate different fluid flow characteristics. For example, the constrictions 1140 or other regions of portions 1164, 1166 may be differently sized such that particles or cells of a first size more readily flow through, if at all, through one of portions 364, 366 as compared to the other of portions 1164, 1166. Because portions 1164, 1166 diverge from opposite sides of central portion 1162, both of portions 1164, 1166 receive fluid directly from portion 1162 without fluid being siphoned to any other portions beforehand.

Each of micro-fabricated integrated sensors 1138 comprises a micro-fabricated device formed upon substrate 1032 within constriction 1140. In one implementation, sensor 1138 comprises a micro-device that is designed to output electrical signals or cause changes in electrical signals that indicate properties, parameters or characteristics of the fluid and/or cells/particles of the fluid passing through constriction 1140. In one implementation, each of sensors 1138 comprises a cell/particle sensor that detects properties of cells or particles contained in a fluid and/or that detects the number of cells or particles in fluid passing across sensor 1138. For example, in one implementation, sensor 1138 comprises an electric sensor which outputs signals based upon changes in electrical impedance brought about by differently sized particles or cells flowing through constriction 1140 and impacting impedance of the electrical field across or within constriction 1140. In one implementation, sensor 1138 comprises an electrically charged high side electrode and a low side electrode formed within or integrated within a surface of channel 1136 within constriction 40. In one implementation, the low side electrode is electrically grounded. In another implementation, low side electrode comprises a floating low side electrode. For purposes of this disclosure, a "floating" low side electrode refers to an electrode having all connecting admittances zero. In other words, the floating electrode is disconnected, not being connected to another circuit or to earth.

Figure 14:
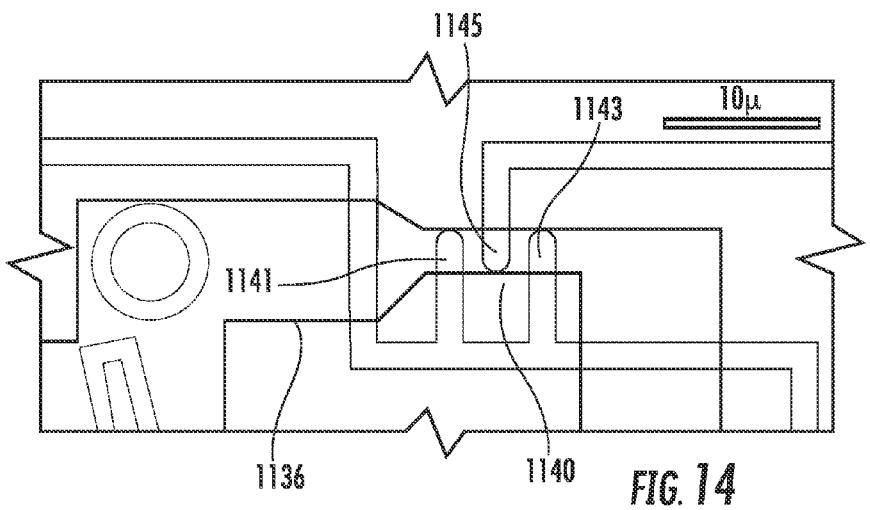
FIG. 14 is a fragmentary top view of an example microfluidic chip, illustrating an example electric sensor within an example microfluidic channel.
Figure 15:
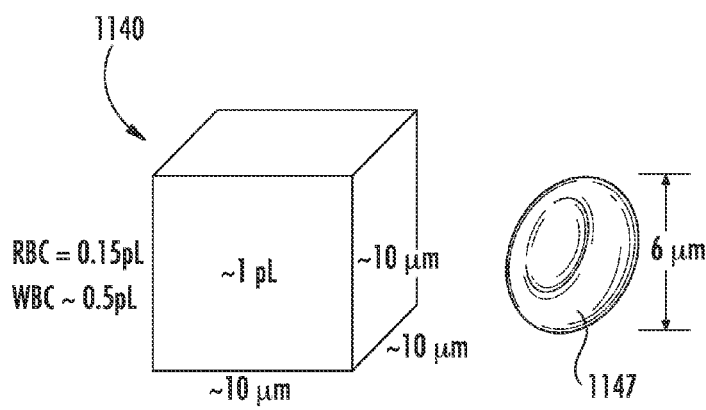
FIG. 15 is a diagram illustrating a volume of an example constriction of a microfluidic channel relative to an example cell.
Figure 16:
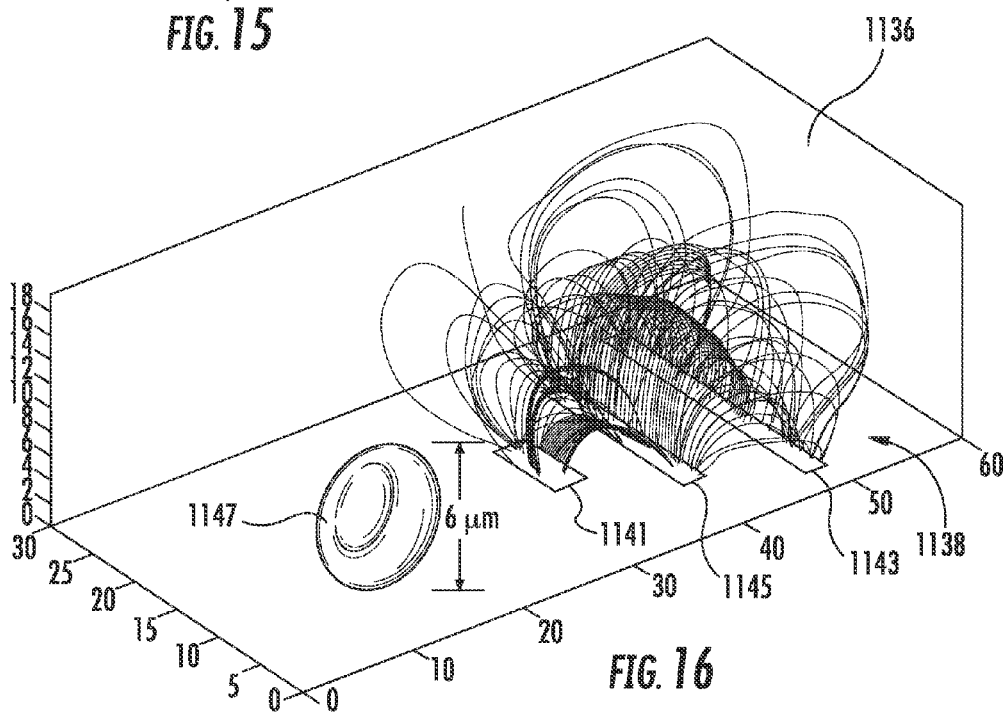
FIG. 16 is a diagram of an example microfluidic channel comprising an example electric sensor, illustrating the creation of an electric field and the relative size of the cell about to pass through the electric field.

FIGS. 14-16 illustrate one example of sensor 1138. As shown by FIG. 14, in one implementation, sensor 1138 comprises an electric sensor comprising low side electrodes 1141, 1143 and charged or active high side electrode 1145. Low side electrodes are either grounded or are floating. Active electrode 1145 is sandwiched between grounding electrodes 143. Electrodes 1141, 1143 and 1145, forming electric sensor 1138, are located within a constriction 1140 formed within channel 1136. Constriction 1140 comprises a region of channel 1136 that has a smaller cross-sectional area than both adjacent regions of channel 36, upstream and downstream of constriction 1140.

FIG. 15 illustrates one example sizing or dimensioning of constriction 1140. Constriction 1140 has a cross-sectional area similar to that of the individual particles or cells that pass through constriction 1140 and which are being tested. In one implementation in which the cells 1147 being tested have a general or average maximum dimension of 6 μm, constriction 1140 has a cross-sectional area of 100 μm². In one implementation, constriction 1140 has a sensing volume of 1000 μm³. For example, in one implementation, constriction 1140 has a sense volume forming a region having a length of 10 μm, a width of 10 μm and a height of 10 μm. In one implementation, constriction 1140 has a width of no greater than 30 μm. The sizing or dimensioning of constriction 1140 restricts the number of particles or individual cells that may pass through constriction 1140 at any one moment, facilitating testing of individual cells or particles passing through constriction 1140.

FIG. 16 illustrates the forming an electric field by the electrodes of electric sensor 1138. As shown by FIG. 16, low side electrodes 1143 share active or high side electrode 1145, wherein an electrical field is formed between active high side electrode 1145 and each of the two low side electrodes 1141, 1143. In one implementation, low side electrodes 1141, 1143 are likely grounded. In another implementation, low side electrode 1141, 1143 comprise floating low side electrodes. As fluid flows across the electrodes 1141, 1143, 1145 and through the electrical field, the particles, cells or other analyte within the fluid impact the impedance of the electrical field. This impedance is sensed to identify characteristics of the cells or particles or to count the number of cells or particles passing through the electric field.

Pump 1160 comprises a device to move fluid through microfluidic channel 1136 and through constrictions 1140 across one of sensors 1138. Pump 1160 draws fluid from microfluidic reservoir 1134 into channel 1136. Pump 1160 further circulates fluid that has passed through constriction 1140 and across sensor 1138 back to reservoir 1134.

In the example illustrated, pump 1160 comprises a resistor actuatable to either of a pumping state or a temperature regulating state. Resistor 60 is formed from electrically resistive materials that are capable of emitting a sufficient amount of heat so as to heat adjacent fluid to a temperature above a nucleation energy of the fluid. Resistor 1160 is further capable of emitting lower quantities of heat so as to heat fluid adjacent resistor 1160 to a temperature below a nucleation energy of the fluid such that the fluid is heated to a higher temperature without being vaporized.

When the resistor forming pump 1160 is in the pumping state, pulses of electrical current passing through the resistor cause resistor to produce heat, heating adjacent fluid to a temperature above a nucleation energy of the adjacent fluid to create a vapor bubble which forcefully expels fluid across constrictions 1140 and back into reservoir 34. Upon collapse of the bubble, negative pressure draws fluid from microfluidic reservoir 1134 into channel 1136 to occupy the prior volume of the collapsed bubble.

When the resistor forming pump 1160 is in the temperature regulating state or fluid heating state, the temperature of adjacent fluid rises to a first temperature below a nucleation energy of the fluid and then maintains or adjusts the operational state such that the temperature of the adjacent fluid is maintained constant or constantly within a predefined range of temperatures that is below the nucleation energy. In contrast, when resistor 1160 is being actuated to a pumping state, resistor 1160 is in an operational state such that the temperature of fluid adjacent the resistor 1160 is not maintained at a constant temperature or constantly within a predefined range of temperatures (both rising and falling within the predefined range of temperatures), but rapidly and continuously increases or ramps up to a temperature above the nucleation energy of the fluid.

In yet other implementations, pump 1160 may comprise other pumping devices. For example, in other implementations, pump 1160 may comprise a piezo-resistive device that changes shape or vibrates in response to applied electrical current to move a diaphragm to thereby move adjacent fluid across constrictions 1140 and back to reservoir 1134. In yet other implementations, pump 1160 may comprise other microfluidic pumping devices in fluid communication with microfluidic channel 1136.

As indicated by arrows in FIG. 13, actuation of pump 1160 to the fluid pumping state moves the fluid sample through central portion 1162 in the direction indicated by arrow 1170. The fluid sample flows through constrictions 1140 and across sensors 1138, where the cells within the fluid sample impact the electric field (shown in FIG. 16) and wherein the impedance is measured or detected to identify a characteristic of such cells or particles and/or to count the number of cells flowing across the sensing volume of sensor 1138 during a particular interval of time. After passing through constrictions 1140, portions of the fluid sample continue to flow back to microfluidic reservoir 1134 as indicated by arrows 1171.

As further shown by FIG. 12, microfluidic chip 1130 additionally comprises temperature sensors 1175, electrical contact pads 1177 and multiplex or circuitry 11 79. Temperature sensors 1175 are located at various locations amongst the sensing regions 1135. Each of temperature sensors 1175 comprises a temperature sensing device to directly or indirectly output signals indicative of a temperature of portions of the fluid sample in the microfluidic channel 1136. In the example illustrated, each of temperature sensors 1135 is located external to channel 36 to indirectly sense a temperature of the sample fluid within channel 1136. In other implementations, temperature sensors 1175 are located within microfluidic reservoir 1134 to directly sense a temperature of the sample fluid within reservoir 1134. In yet another implementation, temperature sensors 1175 are located within channel 1136. In yet other implementations, temperature sensor 240 may be located at other locations, wherein the temperature at such other locations is correlated to the temperature of the sample fluid being tested. In one implementation, temperature sensors 1135 output signals which are aggregated and statistically analyzed as a group to identify statistical value for the temperature of the sample fluid being tested, such as an average temperature of the sample fluid being tested. In one implementation, chip 1130 comprises multiple temperature sensors 1175 within reservoir 1134, multiple temperature sensors 1175 within channel 1136 and/or multiple temperature sensors external to the fluid receiving volume provided by reservoir 1134 and channel 1136, within the substrate of chip 1130.

In one implementation, each of temperature sensors 1175 comprises an electrical resistance temperature sensor, wherein the resistance of the sensor varies in response to changes in temperature such that signals indicating the current electrical resistance of the sensor also indicate or correspond to a current temperature of the adjacent environment. In other implementations, sensors 1175 comprise other types of microfabricated or microscopic temperature sensing devices.

Electrical contact pads 1177 are located on end portions of microfluidic chip 1130 which are spaced from one another by less than 3 mm and nominally less than 2 mm, providing microfluidic chip 1130 with a compact length facilitates the compact size of cassette 1010. Electrical contact pads 1177 sandwich the microfluidic and sensing regions 1135 and are electrically connected to sensors 1138, pumps 1160 and temperature sensors 1175. Electrical contact pads 1177 are further electrically connected to the electrical connectors 1016 of cassette board 1012 (shown in FIGS. 9B, 9C 10A and 10B.

Multiplexer circuitry 1179 is electrically coupled between electrical contact pads 1177 and sensors 1138, pumps 1160 and temperature sensors 1175. Multiplexer circuitry 1179 facilitates control and/or communication with a number of sensors 1138, pumps 1160 and temperature sensors 1175 that is greater than the number of individual electrical contact pads 1177 on chip 430. For example, despite chip 1130 having a number n of contact pads, communication is available with a number of different independent components having a number greater than n. As a result, valuable space or real estate is conserved, facilitating a reduction in size of chip 1130 and cassette 1010 in which chip 1130 is utilized. In other implementations, multiplexer circuitry 1179 may be omitted.

Figure 17:
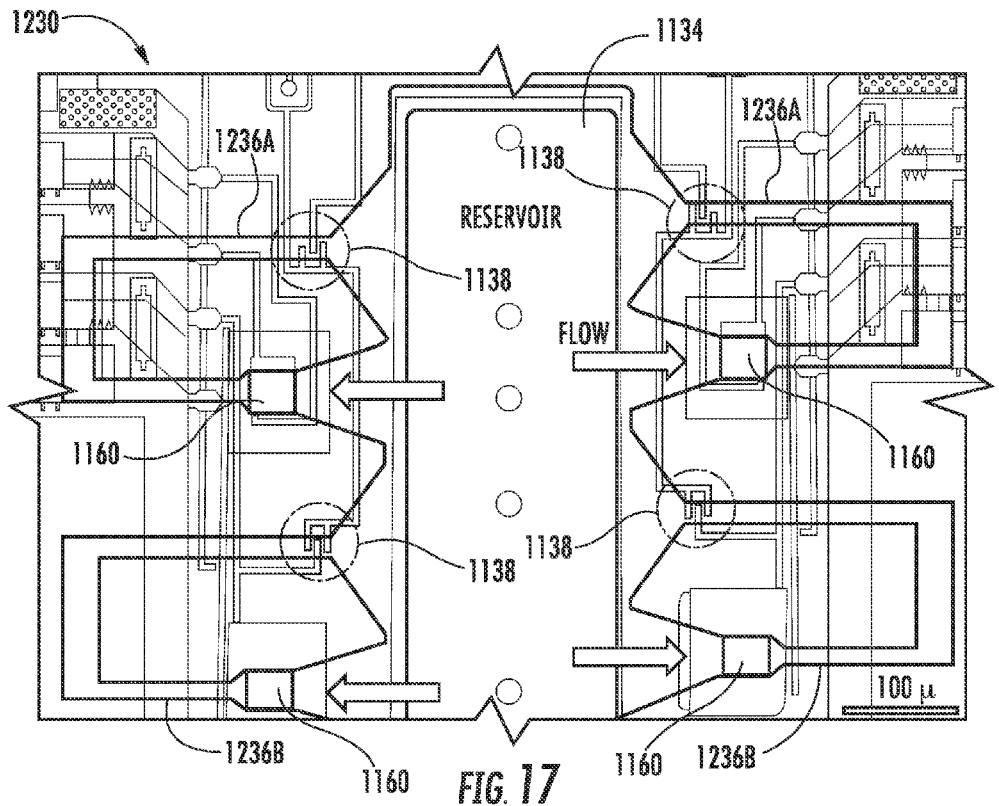
FIG. 17 is a fragmentary top view of another example microfluidic chip usable in the cassette of FIGS. 8 and 9A.

FIG. 17 is an enlarged view of a portion of microfluidic chip 1230, another example implementation of microfluidic chip 1030. Similar to microfluidic chip 1130, microfluidic chip 1430 comprises temperature sensors 1175, electrical contact pads 1177 and multiplexer circuitry 1179 illustrated and described above with respect to microfluidic chip 1130. Like microfluidic chip 1130, microfluidic chip 1230 comprises sensor regions comprising an electric sensor 1138 and a pump 1160. Microfluidic chip 1230 additionally comprises temperature sensors 1175 dispersed throughout. Microfluidic chip 1230 is similar to microfluidic chip 1130 except that microfluidic chip 1230 comprises differently sized or dimensioned microfluidic channels. In the example illustrated, microfluidic chip 1230 comprises U-shaped microfluidic channels 1236A and 1236B (collectively referred to as microfluidic channels 1236). Microfluidic channels 1236A have a first width while microfluidic channels 1236B have a second with less than the first width.

Because microfluidic channels 1236 have different widths or different cross-sectional areas, channels 12 36 receive differently sized cells or particles in the fluid sample for testing. In one such implementation, the different sensors 1138 in the differently sized channels 1236 are operated at different frequencies of alternating current such perform different tests upon the differently sized cells in the differently sized channels 1236. In another of such implementations, the differently sized channels 1236 contain a different type or different electric sensor 1138 to detect different characteristics of the differently sized cells, particles or other analyte passing through the differently sized channels 1236.

Figures 18, 19:
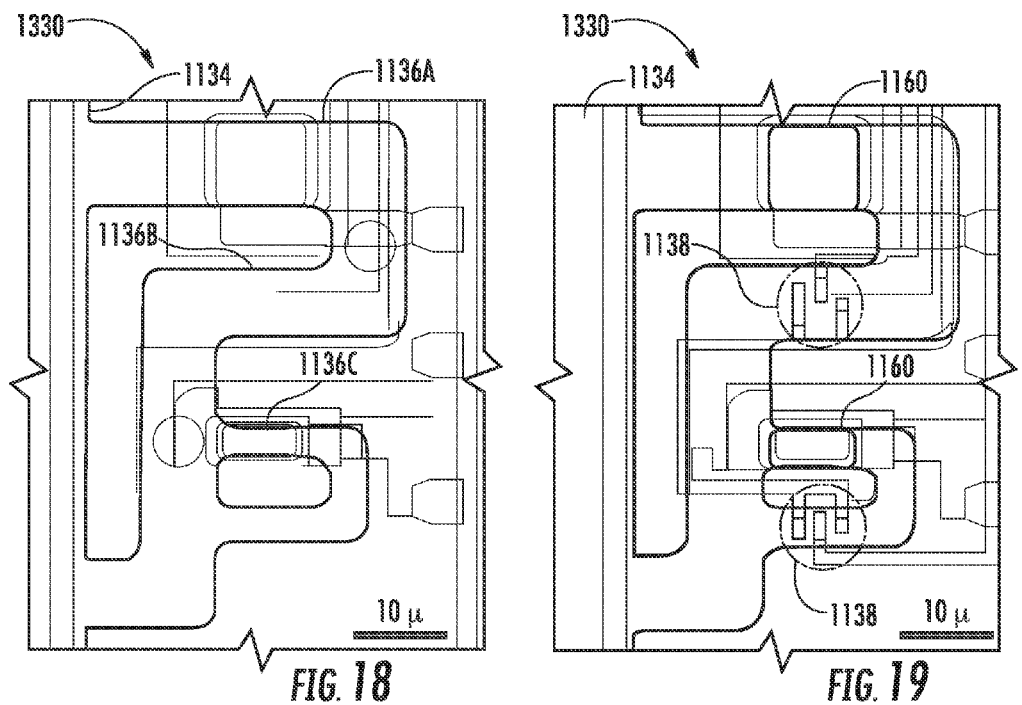
FIG. 18 is a fragmentary top view of another example microfluidic chip usable in the cassette of FIGS. 8 and 9A, illustrating example microfluidic channel portions.
FIG. 19 is a fragmentary top view of the microfluidic chip of FIG. 18 illustrating example pumps and sensors within the microfluidic channel portions.

FIGS. 18 and 19 are enlarged views illustrating a portion of microfluidic chip 1330, another example implementation of microfluidic chip 1030. Similar to microfluidic chip 1130, microfluidic chip 1430 comprises temperature sensors 1175, electrical contact pads 1177 and multiplexer circuitry 1179 illustrated and described above with respect to microfluidic chip 1130. Microfluidic chip 1330 is similar to microfluidic chip 1230 in that microfluidic chip 1330 comprises microfluidic channel portions 1336A, 1336B and 1336C (collectively referred to as channels 1336) of varying widths. Microfluidic chip 1330 has a different geometry as compared to microfluidic chip 1230. As with microfluidic chip 1230, microfluidic chip 1330 comprises various sensing regions with the sensing region including an electric sensor 1138 and a pump 1160.

FIG. 18 omits sensors 1138 and pumps 1160 to better illustrate channels 1336. As shown by FIG. 18, channel portion 1336A has a width greater than the width of channel portion 1336B. Channel portion 1336B has a width greater than the width of channel portion 1336C. Channel portion 1336A extends from microfluidic reservoir 1134. Channel portion 1336B extends from channel portion 1336A and continues back to microfluidic reservoir 1134. Channel portion 1336C branches off of channel portion 1336B and returns to channel portion 1336B. as shown by FIG. 19, pump 1160 is located within channel portion 1336A. Sensors 1138 are located within channel portion 1336B and channel portion 1336C. As a result, a single pump 1160 pumps a fluid sample through both of channel portions 1336B and 1336C across the respective sensors 1138 contained within the differently sized channels. Cells in all of the pumped fluid pass across and are sensed by sensor 1138 in channel portion 1336B. Those cells that are sufficiently small to pass through the narrower channel portion 1336C pass through and are sensed by the sensor 1138 in channel portion 1336C. As a result, the sensor 1138 and channel portion 1336C senses a subset or less than complete portion of the cells and fluid pumped by pump 1160.

Figure 20:
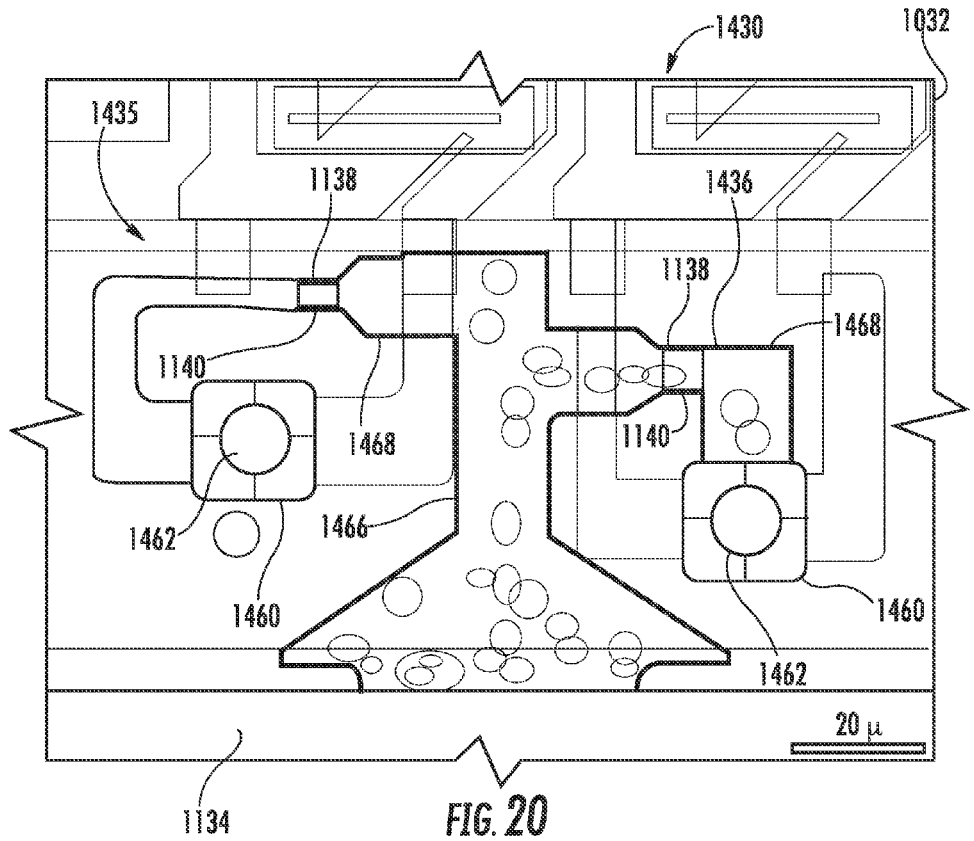
FIG. 20 is a fragmentary top view of another example microfluidic chip usable in the cassette of FIGS. 8 and 9A.

FIG. 20 is an enlarged view of a portion of microfluidic chip 1430, another example implementation of microfluidic chip 1030. Microfluidic chip 1430 is specifically designed for use with a cassette, such as cassette 1010, that comprises a discharge reservoir, such as discharge reservoir 1024 shown in FIG. 9A. Similar to microfluidic chip 1130, microfluidic chip 1430 comprises temperature sensors 1175, electrical contact pads 1177 and multiplexer circuitry 1179 illustrated and described above with respect to microfluidic chip 1130.

FIG. 20 illustrates one example sensing region 1435 of microfluidic chip 1430, wherein microfluidic chip 1430 comprises multiple such sensing regions 1435. Microfluidic sensing region 1435 comprises microfluidic channel 1436, fluid sensors 1138, pumps 1460 and discharge passages 1462. Microfluidic channel 1436 is formed in substrate 1032 and comprises inlet portion 1466 and branch portions 1468. Inlet portion 1466 has a funnel shaped mouth extending from microfluidic reservoir 1134. Inlet portion 466 facilitates inflow of fluid, including cells or particles, into channel 1436 and through each of branch portions 1468.

Branch portions 1468 extend from opposite sides of central portion 1466. Each of branch portions 1468 terminate at an associated discharge passage 1462. In the example illustrated, each of branch portions 1468 comprises a constriction 1140 in which the sensor 1138 is located.

Pumps 1460 are located proximate to and nominally opposite to discharge passages 1462 so as to pump fluid through discharge passages 1462 to the underlying discharge reservoir 1024 (shown in FIG. 9A). Pumps 1460 comprise resistors similar to pumps 1160 described above. In the pumping state, pumps 1460 receive electrical current the heat adjacent fluid to a temperature above a nucleation energy of the fluid so as to create a vapor bubble which pushes fluid between pump 1460 and discharge passage 1462 through discharge passage 1462 into the discharge reservoir 1024. Collapse of the vapor bubble draws portions of a fluid sample from microfluidic reservoir 1134, through central portion 1466 and across sensors 1138 in branch portions 1468.

Discharge passages 1462 extend from a portion of passage 1436 adjacent to pump 460 to discharge reservoir 156. Discharge passages 1462 inhibit reverse or backflow of fluid within discharge reservoir 1024 through discharge passages 1462 back into channel 1436. In one implementation, each of discharge passages 1462 comprises a nozzle through which fluid is pumped by pump 1460 into discharge reservoir 1024. In another implementation, discharge passage 1462 comprises a unidirectional valve.

Referring back to FIG. 7, cassette interface 1200 sometimes referred to as a "reader" or "dongle", interconnects and serves as an interface between cassette 1010 and mobile analyzer 1232. Cassette interface 1200 contains components or circuitry that is dedicated, customized or specifically adapted for controlling components of microfluidic cassette 1010. Cassette interface 1200 facilitates use of a general portable electronic device, loaded with the appropriate program and application program interface, but wherein the portable electronic device may omit the hardware or firmware specifically used to enable control of the components of cassette 1010. As a result, cassette interface 220 facilitates use of multiple different portable electronic devices 1232 which have simply been updated with an upload of an application program and an application programming interface. Cassette interface 1200 facilitates use of mobile analyzer 1232 that are not specifically designated or customized for use just with the particular microfluidic cassette 1010. Said another way, cassette interface 1200 facilitates use of mobile analyzer 1232 with multiple different cassettes 1010 having different testing capabilities through the connection of a different cassette interface 1200.

Cassette interface 220 carries circuitry and electronic components dedicated or customized for the specific use of controlling the electronic components of cassette 1010. Because cassette interface 1200 carries much of the electronic circuitry and components specifically dedicated for controlling the electronic components of cassette 1010 rather than such electronic components being carried by cassette 1010 itself, cassette 1010 may be manufactured with fewer electronic components, allowing the costs, complexity and size of cassette 1010 to be reduced. As a result, cassette 1010 is more readily disposable after use due to its lower base cost. Likewise, because cassette interface 1200 is releasably connected to cassette 210, cassette interface 1200 is reusable with multiple exchanged cassettes 1010. The electronic components carried by cassette interface 1200 and dedicated or customized to the specific use of controlling the electronic components of a particular cassette 1010 are reusable with each of the different cassettes 1010 when performing fluid or blood tests on different fluid samples or fluid samples from different patients or sample donors.

In the example illustrated, cassette interface 1200 comprises electrical connector 1204, electrical connector 1206 and firmware 1208 (schematically illustrated external to the outer housing of interface 1200). Electrical connector 1204 comprises a device by which cassette interface 1200 is releasably electrically connected directly to electrical connectors 1016 of cassette 1010. In one implementation, the electrical connection provided by electrical connector 1204 facilitates transmission of electrical power for powering electronic components of microfluidic chip 1030, 1130, 1230, 1330, 1430, such as electric sensors 1138 or a microfluidic pump 1160. In one implementation, the electrical connection provided by electrical connector 1204 facilitates transmission of electrical power in the form of electrical signals providing data transmission to microfluidic chip 1030, 1130, 1230, 1330, 1430 to facilitate control of components of microfluidic chip 1030, 1130, 1230, 1330, 1430. In one implementation, the electrical connection provided by electrical connector 1204 facilitates transmission of electrical power in the form electrical signals to facilitate the transmission of data from microfluidic chip 1030, 1130, 1230, 1330, 1430 to the mobile analyzer 1232, such as the transmission of signals from sensor sensors 38. In one implementation, electrical connector 1204 facilitates each of the powering of microfluidic chip 1030, 1130, 1230, 1330, 1430 as well as the transmission of data signals to and from microfluidic chip 1030, 1130, 1230, 1330, 1430.

In the example illustrated, electrical connectors 1204 comprise a plurality of electrical contact pads located in a female port, wherein the electrical contact pads which make contact with corresponding pads 1016 of cassette 1010. In yet another implementation, electrical connectors 1204 comprise a plurality of electrical prongs or pins, a plurality of electrical pin or prong receptacles, or a combination of both. In one implementation, electrical connector 1204 comprises a universal serial bus (USB) connector port to receive one end of a USB connector cord, wherein the other end of the USB connector cord is connected to cassette 210. In still other implementations, electrical connector 1204 may be omitted, where cassette interface 1200 comprises a wireless communication device, such as infrared, RF, Bluetooth other wireless technologies for wirelessly communicating between interface 1200 and cassette 1010.

Electrical connector 1204 facilitates releasable electrical connection of cassette interface 1200 to cassette 1010 such that cassette interface 1200 may be separated from cassette thousand 10, facilitating use of cassette interface 1200 with multiple interchangeable cassettes 1010 as well as disposal or storage of the microfluidic cassette 1010 with the analyzed fluid, such as blood. Electrical connectors 1204 facilitate modularization, allowing cassette interface 1200 and associated circuitry to be repeatedly reused while cassette 1010 is separated for storage or disposal.

Electrical connector 1206 facilitates releasable connection of cassette interface 1200 to mobile analyzer 1232. As a result, electrical connector 1206 facilitates use of cassette interface 1200 with multiple different portable electronic devices 1232. In the example illustrated, electrical connector 1206 comprises a universal serial bus (USB) connector port to receive one end of a USB connector cord 1209, wherein the other end of the USB connector cord 1209 is connected to the mobile analyzer 1232. In other implementations, electrical connector 1206 comprises a plurality of distinct electrical contact pads which make contact with corresponding blood connectors of mobile analyzer 1232, such as where one of interface 1200 and mobile analyzer 1232 directly plug into the other of interface 1200 and mobile analyzer 1232. In another implementation, electrical connector 1206 comprises prongs or prong receiving receptacles. In still other implementations, electrical connector 1206 may be omitted, where cassette interface 1200 comprises a wireless communication device, utilizing infrared, RF, Bluetooth or other wireless technologies for wirelessly communicating between interface 1200 and mobile analyzer 1232.

Firmware 1208 comprises electronic componentry and circuitry carried by cassette interface 1200 and specifically dedicated to the control of the electronic components and circuitry of microfluidic chip 1030, 1130, 1230, 1330, 1430 and cassette 1010. In the example illustrated, firmware 1208 serves as part of a controller to control electric sensors 1138.

As schematically shown by FIG. 7, firmware 1208 comprises at least one printed circuit board 1210 which supports frequency source 1212, and impedance extractor 1214 to receive first composite or base signals from the sensors 1138 and to extract impedance signals from the base signals and a buffer 1216 to store the impedance signals as or until the impedance signals are transmitted to mobile analyzer 1232. For example, in one implementation, impedance extractor 1214 performs analog quadrature amplitude modulation (QAM) which utilizes radiofrequency (RF) components to extract the frequency component out so that the actual shift in phase caused by impedance of the device under test (the particular sensor 1138) may be utilized.

Figure 21:
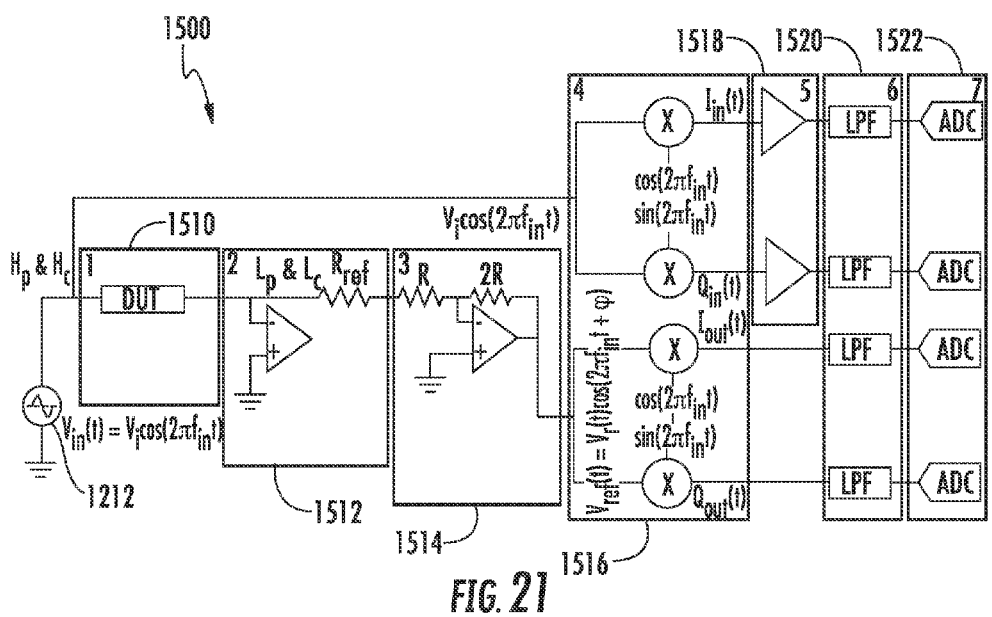
FIG. 21 is a schematic diagram of an example impedance sensing circuit.

FIG. 21 is a schematic diagram of an example impedance sensing circuit 1500 providing frequency source 1212 and impedance extractor 1214. In circuit block 1510, signals are measured from the high and low electrodes in the microfluidic channel 1136 (the device under test (DUT)). In circuit block 1512, the circuitry converts the current through the high low electrodes (device under test) to a voltage. In circuit block 1514, the circuitry conditions the voltage signals so as to have a correct phase and amplitude before and after the mixer, respectively. In circuit block 1516, the circuitry breaks the input and output voltage signals into real and imaginary parts. In circuit block 1518, the circuitry recovers each signal's amplitude. In circuit block 1520, the circuitry filters out high-frequency signals. In circuit block 1522, the circuitry converts the analog signals to digital signals where the digital signals are buffered by buffer 1216, such as with a field programmable gate array.

In one implementation, firmware 1208 comprises a field programmable gate array which serves as a frequency source controller and the buffer 1216. In another implementation, firmware 1208 comprises an application-specific integrated circuit (ASIC) serving as a frequency source controller, the impedance extractor 1214 and the buffer 1216. In each case, raw or base impedance signals from sensors 1138 are amplified and converted by an analog-to-digital converter prior to being used by either the field programmable gate array or the ASIC. In implementations where firmware 1208 comprises a field programmable gate array or an ASIC, the field programmable gate array or ASIC may additionally serve as a driver for other electronic components on microfluidic chip 1010 such as microfluidic pumps 1130 (such as resistors), temperature sensors 1175 and other electronic components upon the microfluidic chip.

Mobile analyzer 1232 comprises a mobile or portable electronic device to receive data from cassette 1010. Mobile analyzer 1232 is releasably or removably connected to cassette 1010 indirectly via cassette interface 1200. Mobile analyzer 1232 performs varies functions using data received from cassette 1010. For example, in one implementation, mobile analyzer 1232 stores the data. In the example illustrated, mobile analyzer 1232 additionally manipulates or processes the data, displays the data and transmits the data across a local area network or wide area network (network 1500) to a remote analyzer 1300 providing additional storage and processing.

In the example illustrated, mobile analyzer 1232 comprises electrical connector 1502, power source 1504, display 1506, input 1508, processor 1510, and memory 1512. In the example illustrated, electrical connector 1502 is similar to electrical connectors 1206. In the example illustrated, electrical connector 1502 comprises a universal serial bus (USB) connector port to receive one end of a USB connector cord 1209, wherein the other end of the USB connector cord 1209 is connected to the cassette interface 1200. In other implementations, electrical connector 1502 comprises a plurality of distinct electrical contact pads which make contact with corresponding electrical connectors of interface 1200, such as where one of interface 1200 and mobile analyzer 1232 directly plug into the other of interface 1200 and mobile analyzer 1232. In another implementation, electrical connector 1206 comprises prongs or prong receiving receptacles. In still other implementations, electrical connector 1502 may be omitted, where mobile analyzer 1232 and cassette interface 1200 each comprise a wireless communication device, utilizing infrared, RF, Bluetooth or other wireless technologies for facilitating wireless communication between interface 1200 and mobile analyzer 1232.

Power source 1504 comprise a source of electrical power carried by mobile analyzer 1232 for supplying power to cassette interface 1200 and cassette 1010. Power source 1504 comprises various power control electronic componentry which control characteristics of the power (voltage, current) being supplied to the various electronic components of cassette interface 1200 and cassette 1010. Because power for both cassette interface 1200 and cassette 1010 are supplied by mobile analyzer 1232, the size, cost and complexity of cassette interface 1200 and cassette 1010 are reduced. In other implementations, power for cassette 1010 and cassette interface 1200 are supplied by a battery located on cassette interface 1200. In yet another implementation, power for cassette 1010 is provided by a battery carried by cassette 1010 and power for interface 1200 is supplied by a separate dedicated battery for cassette interface 1200.

Display 1506 comprises a monitor or screen by which data is visually presented. In one implementation, display 1506 facilitates a presentation of graphical plots based upon data received from cassette 1010. In some implementations, display 1506 may be omitted or may be replaced with other data communication elements such as light emitting diodes, auditory devices are or other elements that indicate results based upon signals or data received from cassette 1010.

Input 1508 comprises a user interface by which a person may input commands, selection or data to mobile analyzer 1232. In the example illustrated, input 1508 comprise a touch screen provided on display 1506. In one implementation, input 1508 may additionally or alternatively utilize other input devices including, but are not limited to, a keyboard, toggle switch, push button, slider bar, a touchpad, a mouse, a microphone with associated speech recognition program and the like. In one implementation, input 1506 facilitates input of different fluid tests or modes of a particular fluid test pursuant to prompts provided by an application program run on mobile analyzer 1232.

Processor 1510 comprises at least one processing unit designed to generate control signals controlling the operation of sensors 1138 as well as the acquisition of data from sensors 1138. Processor 1510 further outputs control signals controlling the operation of pumps 1160 and temperature sensors 1175. In the example illustrated, processor 572 further analyzes data received from chip 230 to generate output that is stored in memory 1512, displayed on display 1506 and/or further transmitted across network 1500 to remote analyzer 1300.

Memory 1512 comprises a non-transitory computer-readable medium containing instructions for directing the operation of processor 1510. As schematically shown by FIG. 7, memory 1512 comprises or stores an application programming interface 1520 and application program 1522. Application programming interface 1520 comprises a library of routines, protocols and tools, which serve as building blocks, for carrying out various functions or tests using cassette 1010. Application programming interface 1520 comprises programmed logic that accesses the library and assembles the "building blocks" or modules to perform a selected one of various functions or tests using cassette 1010. For example, in one implementation, application programming interface 1520 comprises an application programming interface library that contains routines for directing the firmware 1208 to place electric sensors 1138 in selected operational states, such as through the application of different frequencies of alternating current. In the example illustrated, the library also contains routines for directing firmware 1208 to operate fluid pumps 1160 or dynamically adjusts operation of such pumps 1160 or electric sensors 1138 in response to a sensed temperature of the fluid being tested from temperature sensors 1175. In one implementation, mobile analyzer 1232 comprises a plurality of application programming interfaces 1520, each application programming interface 1520 being specifically designed are dedicated to a particular overall fluid or analyte test. For example, one application programming interface 1520 may be directed to performing cytology tests. Another application program interface 1520 may be directed to performing coagulation tests. In such implementations, the multiple application programming interfaces 1520 may share the library of routines, protocols and tools.

Application programming interface 1520 facilitates testing of fluids using cassette 1010 under the direction of different application programs. In other words, application programming interface 1520 provides a universal programming or machine-readable set of commands for firmware 1208 that may be used by any of a variety of different application programs. For example, a user of mobile analyzer 1232 is able to download or install any of a number of different application programs, wherein each of the different application programs is designed to utilize the application program interface 1520 so as to carry out tests using cassette 1010. As noted above, firmware 1208 interfaces between application programming interface 1520 and the actual hardware or electronic componentry found on the cassette 1010 and, in particular, microfluidic chip 1030, 1130, 1230, 1330, 1430.

Application program 1522 comprises an overarching program contained in memory 1512 that facilitates user interaction with application programming interface 1520 or the multiple application programming interfaces 1520 stored in memory 1512. Application program 1522 presents output on display 1506 and receives input through input 1508. Application program 1522 communicates with application program interface 1520 in response to input received through input 1508. For example, in one implementation, a particular application program 1522 presents graphical user interfaces on display 1506 prompting a user to select which of a variety of different testing options are to be run using cassette 1010. Based upon the selection, application program 1522 interacts with a selected one of the application programming interfaces 1520 to direct firmware 1208 to carry out the selected testing operation using the electronic componentry of cassette 1010. Sensed values received from cassette 1010 using the selected testing operation are received by firmware 1208 and are processed by the selected application program interface 1520. The output of the application programming interface 1520 is generic data, data that is formatted so as to be usable by any of a variety of different application programs. Application program 1522 presents the base generic data and/or performs additional manipulation or processing of the base data to present final output to the user on display 1506.

Although application programming interface 1520 is illustrated as being stored in memory 1512 along with the application program 1522, in some implementations, application programming interface 1520 is stored on a remote server or a remote computing device, wherein the application program 1522 on the mobile analyzer 1232 accesses the remote application programming interface 1520 across a local area network or a wide area network (network 1500). In some implementations, application programming interface 1520 is stored locally on memory 1512 while application program 1522 is remotely stored a remote server, such as server 1300, and accessed across a local area network or wide area network, such as network 1500. In still other implementations, both application programming interface 1520 and application program 1522 are contained on a remote server or remote computing device and accessed across a local area network or wide area network (sometimes referred to as cloud computing).

In the example illustrated, system 1000 facilitates a reduction in size of chip 1130 by utilizing multiplexer circuitry with the provision of multiplexer circuitry 1179 and associated multiplexer circuitry on interface 1200 or mobile analyzer 1232. System 1000 further facilitates the reduction in size a chip 1130 through the appropriate allocation of the total transmission bandwidth of chip 1130 amongst the different controlled devices of chip 1130, such as fluid sensors 1138, pumps 1140 and temperature sensors 1175. Transmission bandwidth comprises the total capacity for the transmission of signals across and between connectors of port 1204 and 1177. Processor 1510 allocates the total transmission bandwidth by controlling the timing and rate at which control signals are output and sent across connectors of port 1204 and connectors of 1177 to the various controlled devices fluid sensors 1138, pumps 1160 and temperature sensors 1175 as well the timing and rate at which controlled devices are polled for data signals or at which data is received from the controlled devices. Instead of equally apportioning such bandwidth amongst all the controlled devices 1138, 1160, 1175 or amongst the different types or classes of controlled devices such as fluid sensors, temperature sensors and pumps, processor 1510, following instructions contained in memory 1512, differently allocates the transmission bandwidth amongst the different controlled devices.

The different allocation of the total transmission bandwidth across the controlled devices 1138, 1160, 1175 is based upon the class of controlled device or the generic function being performed by the different controlled devices. For example, in one implementation, a first portion of the total transmission bandwidth is allocated to sensors 1138, a second portion, different than the first portion, of the total transmission bandwidth is allocated to temperature sensors 1175 and a third portion of the total transmission bandwidth, different from the first portion and a second portion, is allocated to pumps 1160. In one implementation, the first portion of the total transmission bandwidth allocated to sensors 1138 is uniformly or equally apportioned amongst the different individual sensors 1138, the second portion of the total transmission bandwidth allocated to temperature sensors 1175 is uniformly or equally apportioned amongst the different individual temperature sensors 1175 and the third portion of the total transmission bandwidth allotted to pumps 1160 is uniformly or equally apportioned amongst different individual controlled devices 1160.

In another implementation, the first portion, the second portion and the third portion of the total transmission bandwidth are each non-uniformly or unequally apportioned amongst the individual controlled devices of each class 1138, 1175, 1160 of the controlled devices. In one implementation, different fluid sensors 1138 operate differently, to form different tests upon a fluid sample. For example, in one implementation in which sensors 1138 comprise electric sensors, one of fluid sensors 1138 is provided with a first frequency of alternating current while another of the fluid sensors 1138 is provided with a second different frequency of alternating current such that the two sensors output signals that indicate different parameters are characteristics of the cells or particles being sensed. In such an implementation, processor 1510 allocates each of the different sensors with a different percentage or portion of the total transmission bandwidth based upon the different tests or based on the different frequencies of alternating current being applied to the different sensors.

In one implementation, the allocation or apportionment of the total transmission bandwidth amongst individual controlled devices is additionally based upon characteristics of the individual controlled device itself relative to other controlled devices in the same class devices. For example, in one implementation, different sensors 1138 are located within differently sized constrictions. Such differently sized constrictions may result in a different concentration of cells or particles in the fluid flowing across or through the constriction, a different frequency at which cells are particles flow through the constriction or a different fluid flow rate across the constriction, the geometry of the portion of the fluid channel 1136 in which the sensors 1138 are located. In one implementation, those sensors 1138 located within constrictions having a greater fluid flow rate or a greater frequency at which cells or particles flow across such sensors are allocated a greater percentage of the total transmission bandwidth apportioned to the class of sensors as compared to other of such sensors in the class that are located within constrictions having lower fluid flow rates or a lower frequency at which cells are particles flow across such sensors.

Likewise, in some implementations, different pumps 1160 are located in differently sized and shaped microfluidic channels 1136, different portions of a channel 1136 with different geometries. As a result, the fluid flow or pumping demands placed upon the different pumps 1160 may also differ. In such implementations, those particular pumps 1160 having greater pumping demands are allocated a greater percentage of the total transmission bandwidth apportioned to the class of pumps as compared to other of such pumps in the class that located within channels 1136 that have lesser pumping demands. For example, in one implementation, a pump which is to move fluid through a longer microfluidic channel or a more tortuous microfluidic channel is provided with a greater percentage of the total transmission bandwidth to allow more frequent pulses and more frequent pumping as compared to another pump which is to move fluid through a shorter microfluidic channel or less tortuous microfluidic channel.

In one implementation, processor 1510 allocates a total transmission bandwidth such that processor 1510 polls and receives data from each of the sensors 1138 at a frequency of at least once every 2 μs. In such an implementation, processor 1510 transmits pulses to pumps 1160, comprising resistors, at a frequency of at least once every 100 μs not more frequent than once every 50 μs. In such an implementation, processor 1510 polls and receives data signals from temperature sensors 1175 at a frequency of at least once every 10 ms and not more frequent than once every 1 ms. In yet other implementations, other total transmission bandwidth allocations are employed.

In one implementation, processor 1510 flexibly or dynamically adjust the bandwidth allocation amongst the different controlled devices 138 based upon signal quality/resolution. For example, if a first amount of bandwidth allocated to impedance sensing by sensor 1138 is insufficient because the cells or other analyte are moving past sensor 1138 too fast such that the signal quality/resolution fails to satisfy a predetermined stored signal quality/resolution threshold, processor 1510 may automatically or in response to suggesting a bandwidth allocation increase to the user and receiving authorization from the user, increase the bandwidth allocation to the particular sensor 1138. Conversely, if a particular sensor 1138 has a lower fluid or cell flow rate due to the pumping rate, such that the allocated bandwidth exceeds the amount for achieving satisfactory signal quality/resolution, processor 1510 automatically, or responses suggesting a bandwidth allocation decrease of the user and receiving authorization from the user, decrease the bandwidth allocation to the particular sensor, wherein processor 1510 allocates the now freed bandwidth to another one of sensors 1138.

In the example illustrated in which sensors 1138 comprise electric sensors, application program 1522 and application programming interface 1520 cooperate to direct processor 1510 to control the frequency of the alternating current being applied to each of the sensors 1138 on-chip 1130. With respect to each individual sensor 1138, processor 1510 is directed to apply different non-zero frequencies of alternating current to an individual sensor 1138. In one implementation, processor 1510 dynamically adjusts the frequency of alternating current being applied to electric sensor 1138 based upon real time are ongoing performance of electric sensor 1138 to improve system performance. For example, in one implementation, controller 1510 outputs control signals that apply a first non-zero frequency of alternating current to a selected electric sensor 1138. Based upon signals received from the selected electric sensor 1138 during the application of the first non-zero frequency of alternating current, controller 1510 adjusts the value of the subsequently applied frequency of alternating current applied to electric sensor 1138. Processor 1510 outputs control signals such that frequency source 1212 applies a second non-zero frequency of alternating current to the selected electric sensor 1138, wherein a value of the second non-zero frequency of alternating current applied by frequency source 1212 to the selected electric sensor 1138 is based upon signals received from the electric sensor 1138 during the application of the first non-zero frequency of alternating current.

In one implementation, processor 1510 selectively applies different non-zero frequencies of alternating current to perform different tests upon the fluid sample. As a result of processor 1510 causing frequency source 1212 to apply different non-zero frequencies of alternating current to the electric sensor 1138, the electric sensor 1138 performs different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially bio-hazardous waste is also reduced.

In one implementation, application program 1522 directs processor 1510 to prompt a user for selection of a particular fluid test to be carried out by system 1000. In one implementation, application program 1522 causes processor 1510 to display on display 1506, for selection by user, different names of different tests or the characteristics or cell/particle parameters for selection. For example, processor 1510 may display cell count, cell size or some other parameter for selection by the user using input 1508.

In one implementation, prior to prompting a user for selection of a particular fluid test, application program 1522 to direct processor 1510 to carry out a check with the fluid testing device providing electric sensor 1138 to determine or identify what fluid tests or what frequency ranges are available or for which the fluid testing device is capable of providing. In such an implementation, program 1522 automatically eliminates those fluid tests that cannot be provided by the particular cassette 1010 from the list or menu of possible choices of fluid tests being presented to the user. In yet another implementation, application program 1522 presents a full menu of fluid tests, but notifies the user of those particular fluid tests that are not presently available or selectable given the current cassette 1010 connected to analyzer 1232.

Based upon the received selection for the fluid test to be carried out, processor 1510, following instructions contained in application program 1522, selects a scan range of frequencies of alternating current which is to be crossed or covered during testing with the electric sensor 1138. The scan range is a range across which multiple different frequency of alternating current are to be applied to electric sensor 38 according to a predefined scan profile. The scan range identifies the endpoints for a series of different frequencies of alternating current to be applied to electric sensor 1138 during testing. In one implementation, a scan range of 1 kHz to 10 MHz is applied to a sensor 1138.

The scan profile indicates the specific AC frequency values between the endpoints of the range and their timing of their application to electric sensor 1138. For example, a scan profile may comprise a continuous uninterrupted series of AC frequency values between the endpoints of the scan range. Alternatively, a scan profile may comprise a series of intermittent AC frequency values between the endpoints of the scan range. The number, time interval spacing between different frequencies and/or the incrementing of the frequency values themselves may be uniform or non-uniform in different scan profiles.

In one implementation or user selected mode of operation, processor 1510 carries out the identified scan range and scan profile to identify a frequency that provides the greatest signal-to-noise ratio for the particular testing carried out. After a fluid sample is added and portions of the fluid sample have reached a sense zone and have been detected at the sense zone, the associate pump 1160 is deactivated such that the analyte (cell or particle) is static or stationary in the sense zone of the adjacent sensor 1138. At this time, processor 1510 carries out the scan. During the scan, the frequency of alternating current applied to the particular sensor 1138 which results in the greatest signal-to-noise ratio is identified by processor 1510. Thereafter, pump 1160 which pumps fluid across the particular sensor 1138 is once again activated and the fluid sample is tested using the sensor 1138 with the identified frequency of alternating current being applied to the sensor 1138. In another implementation, a predetermined nominal frequency of alternating current is identified based upon the particular fluid test being performed, wherein multiple frequencies around the nominal frequency are applied to sensor 1138.

In one implementation or user selected mode of operation, processor 1510 identifies the particular range most suited for the fluid test selected by the, wherein the scan profile is a default profile, being the same for each of the different ranges. In another implementation or user selected mode of operation, processor 1510 automatically identifies the particular scan range most suited for the selected fluid test, wherein the user is prompted to select a scan profile. In another implementation or user selected mode of operation, processor 1510, following instructions provided by application program 1522, automatically identifies not only the most appropriate range for the particular fluid test selected by the user, but also the particular scan profile for the particular range for the particular fluid test selected by the user. In still another implementation or user selectable mode of operation, the user is prompted to select a particular scan profile, wherein processor 1510 identifies the most appropriate scan range, given the selected scan profile for the particular selected fluid test. In one implementation, memory 1512, or a remote memory, such as memory 1604, contains a lookup table which identifies different scan ranges in different scan profiles for different available or selectable fluid tests or fluid/cell/particle parameters for which a fluid test may be performed.

One implementation in which sensors 1138 comprise electric sensors, application program interface 1520 and application program 1522 cooperate to direct processor 1510 to apply different frequencies of alternating current to different sensors 1138 on the same microfluidic chip 1130 of cassette 1010. In one implementation, processor 1510 provides user selection of the different non-zero frequencies of alternating current applied to the different electric sensors 38. Because processor 1510 directs frequency source 1512 applies different non-zero frequencies of alternating current to the different electric sensors 1138, the different electric sensors 1138 perform different tests, outputting different signals that may indicate different properties or characteristics of the fluid, or cells contained therein. Such different tests are performed on a single fluid sample on a single fluid testing platform without the fluid sample having to be transferred from one testing device to another. As a result, integrity the fluid sample is maintained, the cost and complexity of performing the multiple different tests is reduced and the amount of potentially biohazardous waste is also reduced.

In the example illustrated, application program 1522 and application programming interface 1520 further cooperate to direct processor 1510 to regulate the temperature of the fluid sample being tested by cassette 1010. Application program 1522, application programming interface 1520 and processor 1510 serve as a controller that facilitates the dual-purpose functioning of resistors serving as pumps 1160 to achieve both fluid pumping and fluid temperature regulation. In particular, processor 1510 actuates resistor to a fluid pumping state by outputting control signals causing a sufficient amount of electrical current to pass through pump 1160 such that resistor of pump 1160 heats adjacent fluid within a microfluidic channel 1136, 1236, 1336, 1436 to a temperature above a nucleation energy of the fluid. As a result, the adjacent fluid is vaporized, creating a vapor bubble having a volume larger than the volume of the fluid from which the vapor bubble was formed. This larger volume serves to push the remaining fluid that was not vaporized within the channel to move the fluid across sensor 1138 or the multiple senses 1138. Upon collapse of the vapor bubble, fluid is drawn from reservoir 1134 into the channel to occupy the previous volume of the collapsed paper bubble. Processor 1510 actuates the resistor of pump 1160 to the pumping state in an intermittent or periodic fashion. In one implementation, processor 1510 actuates the resistor of pump 1160 to the pumping state in a periodic fashion such that the fluid within the microfluidic channel is continuously moving or continuously circulating.

During those periods of time that the resistor of pump 1160 is not being actuated to the pumping state, to a temperature above the nucleation energy of the fluid, processor 1510 uses the same resistor of pump 1160 to regulate the temperature of the fluid for at least those periods the time that the fluid is extending adjacent to or opposite to sensor 1138 and is being sensed by sensor 1138. During those periods the time that resistor 1160 is not in the pumping state, processor 1510 selectively actuates the resistor of pump 1160 to a temperature regulation state in which adjacent fluid is heated without being vaporized. Processor 1510 actuates resistor of pump 1160 to a fluid heating or temperature regulating state by outputting control signals causing a sufficient amount of electrical current to pass through resistor of pump 1160 such that the resistor of pump 1160 heats adjacent fluid within the microfluidic channel to a temperature below a nucleation energy of the fluid, without vaporizing the adjacent fluid. For example, in one implementation, controller actuates resistor to an operational state such that the temperature of adjacent fluid rises to a first temperature below a nucleation energy of the fluid and then maintains or adjusts the operational state such that the temperature of the adjacent fluid is maintained constant or constantly within a predefined range of temperatures that is below the nucleation energy. In contrast, when the resistor of pump 1160 is being actuated to a pumping state, pump 1160 is in an operational state such that the temperature of fluid adjacent the resistor of pump 1160 is not maintained at a constant temperature or constantly within a predefined range of temperatures (both rising and falling within the predefined range of temperatures), but rapidly and continuously increases or ramps up to a temperature above the nucleation energy of the fluid.

In one implementation, processor 1510 controls the supply of electrical current across the resistor of pump 1160 such that the resistor operates in a binary manner when in the temperature regulating state (the temperature of the adjacent fluid is not heated to a temperature above its nucleation energy). In implementations where the resistor of pump 1160 operates in a binary manner in the temperature regulating state, the resistor of pump 1160 is either "on" or "off". When the resistor of pump 1160 is "on", a predetermined amount of electrical current is passed through the resistor of pump 1160 such the resistor of pump 1160 emits a predetermined amount of heat at a predetermined rate. When the resistor of pump 1160 is "off", electrical current is not passed through the resistor such that resistor does not generate or emit any additional heat. In such a binary temperature regulating mode of operation, processor 1510 controls the amount of heat applied to the fluid within my clinic channel by selectively switching the resistor of pump 1160 between the "on" and "off" states.

In another implementation, processor 1510 controls or sets the resistor of pump 1160 at one of a plurality of different "on" operational states when in the temperature regulation state. As a result, processor 1510 selectively varies the rate at which heat is generated and emitted by the resistor of pump 1160, the heat emitting rate being selected from amongst a plurality of different available non-zero heat emitting rates. For example, in one implementation, Processor 1510 selectively varies or controls a rate at which heat is amended by the resistor of pump 1160 by adjusting a characteristic of pump 1160. Examples of a characteristic of the resistor of pump 1160 (other than an on-off state) that may be adjusted include, but are not limited to, adjusting a non-zero pulse frequency, a voltage and a pulse width of electrical current supplied across the resistor. In one implementation, Processor 1510 selectively adjusts multiple different characteristics to control or regulate the rate at which heat is being emitted by the resistor of pump 1160.

In one user selectable operational mode, processor 1510, following instructions from application programming interface 1520 and application program 52, selectively actuates the resistor of pump 1160 to the temperature regulating state to maintain a constant temperature of the fluid below the nucleation energy of the fluid or to maintain a temperature of the fluid constantly within a predefined range of temperatures below the nucleation energy in the fluid according to a predefined or predetermined schedule. In one implementation, the predetermined schedule is a predetermined periodic or time schedule. For example, through historical data collection regarding particular temperature characteristics of fluid testing system 1000, it may have been discovered that the temperature of a particular fluid sample in fluid testing system 1000 undergoes changes in temperature in a predictable manner or pattern, depending upon factors such as the type of fluid being tested, the rate/frequency at which the resistor of pump 1160 is being actuated to the pumping state, the amount of heat emitted by temperature regulator 60 during a pumping cycle in which an individual vapor bubble is created, the thermal properties, thermal conductivity, of various components of fluid testing system 1000, the spacing of the resistor of pump 1160 and sensor 1138, the initial temperature of the fluid sample when initially deposited into sample input port 1018 or into testing system 1000 and the like. Based upon the prior discovered predictable manner or pattern at which the fluid sample undergoes changes in temperature or temperature losses in system 1000, Processor 1510 outputs control signals selectively controlling when the resistor of pump 1160 is either on or off as described above and/or selectively adjusting the characteristic of the resistor of pump 1160 or multiple pumps 1160 when the resistor of pump 1160 is in the "on" state so as to adapt to the discovered pattern of temperature changes or loss and so as to maintain a constant temperature of the fluid below the nucleation energy of the fluid or to maintain a temperature of the fluid constantly within a predefined range of temperatures below the nucleation energy. In such an implementation, the predefined periodic timing schedule at which processor 1510 actuates the resistor of pump 1160 to a temperature regulation state and at which processor 1510 selectively adjusts an operational characteristic of resistor to adjust the heat emitting rate of the resistor of pump 1160 is stored in memory 1512 or is programmed as part of an integrated circuit, such as an application-specific integrated circuit.

In one implementation, the predefined timing schedule at which processor 1510 actuates pump 1160 to the temperature regulating state and at which processor 1510 adjusts the operational state of pump 1160 in the temperature regulating state is based upon or is triggered by insertion of a fluid sample into testing system 1000. In another implementation, the predefined timing schedule is based upon or triggered by an event associated with the pumping of the fluid sample by the resistor of pump 1160. In yet another implementation, the predefined timing schedule is based upon or triggered by the output of signals or data from sensor 1138 or the schedule or frequency at which sensor 1138 is to sense the fluid and output data.

In another user selectable mode of operation, processor 1510 selectively actuates the resistor of pump 1160 to the temperature regulating state and selectively actuates the resistor of pump 1160 to different operational states while in the temperature regulating state based upon signals from temperature sensors 1175 indicating the temperature of the fluid being tested. In one implementation, Processor 1510 switches the resistor of pump 1160 between the pumping state and the temperature regulating state based upon received signals received from temperature sensors 1175 indicating a temperature of the fluid being tested. In one implementation, processor 1510 determines the temperature the fluid being tested based upon such signals. In one implementation, processor 1510 operates in a closed loop manner in which processor 1510 continuously or periodically adjusts the operational characteristic of the resistor of pump 1160 in the temperature regulating state based upon fluid temperature indicating signals being continuously or periodically received from a sensor 1175 or more than one sensor 1175.

In one implementation, processor 1510 correlates or indexes the value of the signals received from temperature sensors 1175 to corresponding operational states of the resistor of pump 1160 and the particular times at which such operational states of the resistor were initiated, the times which such operational state of the resistor were ended and/or the duration of such operational states of the resistor of pump 1160. In such an implementation, processor 1510 stores the indexed fluid temperature indicating signals and their associated resistor operational state information. Using the stored indexed information, processor 1510 determines or identifies a current relationship between different operational states of the resistor pump 1160 and the resulting change in temperature of the fluid within the microphone a channel. As a result, processor 1510 identifies how the temperature of the particular fluid sample or a particular type of fluid within the microfluidic channel respond to changes in the operational state of the resistor pump 1160 in the temperature regulation state. In one implementation, processor 1510 presents the displayed information to allow an operator to adjust operation of testing system 1000 to account for aging of the components of testing system 1000 or other factors which may be affecting how fluid response to changes in operational characteristics of the resistor of pump 1160. In another implementation, processor 1510 automatically adjusts how it controls the operation of the resistor of pump 1160 in the temperature regulating state based upon the identified temperature responses to the different operational state of the resistor. For example, in one implementation, processor 1510 adjusts the predetermined schedule at which the resistor of pump 1160 is actuated between the "on" and "off" states or is actuated between different "on" operational states based upon the identified and stored thermal response relationship between the fluid sample and the resistor. In another implementation, processor 1510 adjusts the formula or formula controlling how processor 1510 responds in real time to temperature signals received from temperature sensors 1175.

Although, in the example illustrated, mobile analyzer 1232 is illustrated as comprising a tablet computer, in other implementations, mobile analyzer 1232 comprises a smart phone or laptop or notebook computer. In yet other implementations, mobile analyzer 1232 is replaced with a stationary computing device, such as a desktop computer or all-in-one computer.

Remote analyzer 1300 comprises a computing device remotely located with respect to mobile analyzer 1232. Remote analyzer 1300 is accessible across network 1500. Remote analyzer 1300 provides additional processing power/speed, additional data storage, data resources and, in some circumstances, application or program updates. Remote analyzer 1300 (schematically shown) comprises communication interface 1600, processor 1602 and memory 1604. Communication interface 1600 comprise a transmitter that facilitates communication between remote analyzer 1300 and mobile analyzer 1232 across network 1500. Processor 1602 comprises a processing unit that carries out instructions contained in memory 1604. Memory 1604 comprises a non-transitory-computer-readable medium containing machine readable instruction, code, program logic or logic encodings that direct the operation of processor 1602. Memory 1604 further to store data or results from the fluid testing performed by system 1000.

Figure 22:
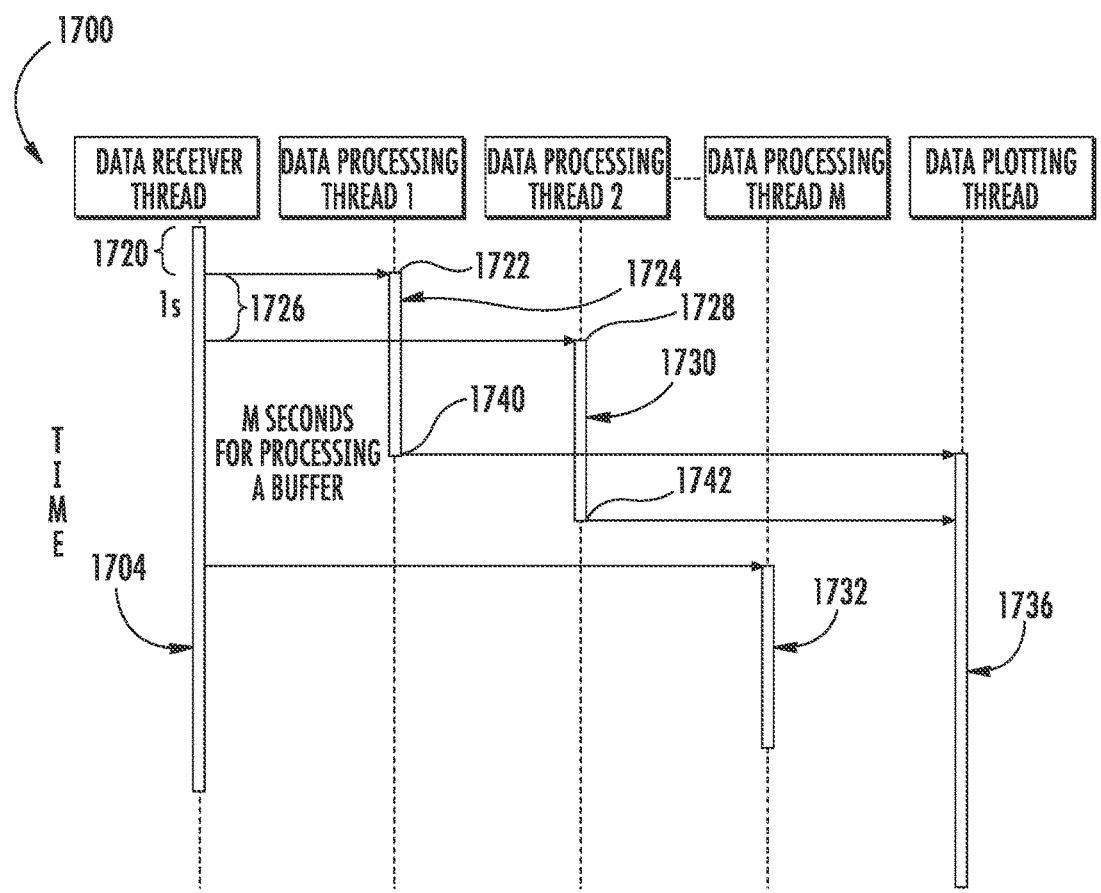
FIG. 22 is a diagram illustrating an example multi-threading method carried out by the fluid testing system of FIG. 7.

As further shown by FIG. 7, memory 1512 additionally comprises buffer module 1530, data processing module 1532 and plotting module 1534. Modules 1530, 1532 and 1534 comprise programs, routines alike which cooperate to direct processor 1510 to carry out and multi-threaded fluid parameter processing method as diagrammed in FIG. 22. FIG. 22 illustrates and describes the reception and processing of a single data receiver thread 1704 by processor 1510. In one implementation, the multi-threaded fluid parameter processing method 1700 is concurrently performed by processor 1510 for each of multiple concurrent data receiver threads in which multiple data sets are concurrently being received. For example, in one implementation, processor 1510 concurrently receives data signals representing sets of data regarding electrical parameters, thermal parameters and optical parameters. For each data set or series of signals for different parameters being received, processor 1510 concurrently carries out method 1700. All of such data sets being concurrently received, buffered, analyzed and then plotted or otherwise presented or displayed on mobile analyzer 1232.

During testing of a fluid sample, such as a blood sample, processor 1510 continuously executes a data receiver thread 1704 in which signals indicating at least one fluid characteristic are received by processor 1510. In one implementation, the signals received by processor 1510 pursuant to the data receiver thread 104 comprise foundational data. For purposes of this disclosure, the term "foundational data", "foundational signals", "foundational fluid parameter data" or "foundational fluid parameter signals" refers to signals from fluid sensor 1138 that have solely undergone modifications to facilitate use of such signals such as amplification, noise filtering or removal, analog-to-digital conversion and, in the case of impedance signals, quadrature amplitude modulation (QAM). QAM utilizes radiofrequency (RF) components to extract the frequency component out so that the actual shift in phase caused by impedance of the device under test (the particular sensor 1138) is identified.

In one implementation, the signals continuously received by processor 1510 during execution of the data receiver thread 1704 comprise electrical impedance signals indicating changes in electrical impedance resulting from the flow of the fluid through art across an electric field region. The signals continuously received by processor 1510 during execution of the data receiver thread 1704 comprise foundational data, meaning that such signals have undergone various modifications to facilitate subsequent use and processing of such signals as described above. In one implementation, data receiver thread 1704, carried out by processor 1510, receives the foundational impedance data or foundational impedance signals at a rate of at least 500 kHz.

During reception of the foundational fluid parameter signals under the data receiver thread 1704, buffer module 1530 directs processor 1510 to repeatedly buffer or temporarily store a predetermined time quantity of foundational signals. In the example illustrated, buffer module 1530 directs processor 1510 to repeatedly buffer or temporarily store in a memory, such as memory 1512 or another memory, all of the foundational fluid parameter signals received during a one second interval or period of time. In other implementations, the predetermined time quantity of foundational signals comprises all the foundational fluid parameter signals received during a shorter or during a longer period of time.

Upon completion of the buffering of each predetermined time quantity of signals, data processing module 1532 directs processor 1510 to initiate and carry out a data processing thread that executes on each of the foundational fluid parameter signals buffered in the associated and just completed time quantity of foundational fluid parameter signals. As diagrammed in the example of FIG. 3, after the foundational fluid parameter signals, such as impedance signals, have been received from cassette interface 1200 for the first predetermined period of time 1720 and buffered, data processing module 1532 directs processor 1510, at time 1722, to initiate a first data processing thread 724 during which each of the foundational fluid parameter signals received during period of time 1720 are processed or analyzed. For purposes of this disclosure, the terms "process" or "analyze" with reference to foundational fluid parameter signals refers to additional manipulation of the foundational fluid parameter signals through the application of formulas and the like, beyond acts such as amplification, noise reduction or removal or modulation, to determine or estimate actual properties of the fluid being tested. For example, processing or analyzing foundational fluid parameter signals comprises using such signals to estimate or determine a number of individual cells in a fluid at a time or during a particular period of time, or to estimate or determine other physical properties of the cells or of the fluid itself, such as the size of cells or the like.

Likewise, after fluid parameter signals from fluid testing device have been received and buffered for the second predetermined period of time 1726, which consecutively follows the first period of time 1720, data processing module 1532 directs processor 1510 at time 1728, to initiate a second data processing thread 1730 during which each of the foundational fluid parameter signals received during the period of time 1726 are processed or analyzed. As indicated in FIG. 22 and the illustrated data processing thread 1732 (data processing thread M), the described cycle of buffering a predetermined time quantity of signals and then, upon the expiration of the time quantity or period of time, initiating an associated data thread to act upon or process the signals received during the period of time is continuously repeated as the data receiver thread 1704 continues to receive fluid parameter data signals from cassette interface 1200.

Upon completion of each data processing thread, the processed signals or data results are passed or transferred to a data plotting thread 1736 as diagrammed in FIG. 22. In the example illustrated, upon completion of processing of the fluid parameter signals received during the period of time 1720 at time 1740, the results or process data from such processing or analysis are transmitted to data plotting thread 1736, wherein the results are incorporated into the ongoing plotting being carried out by data plotting thread 1736 under the direction of plotting module 1534. Likewise, upon completion of the processing of the fluid parameter signals that were received during the period of time 1726 at time 1742, the results or process data from such processing or analysis are transmitted to data plotting thread 1736, wherein the results are incorporated into the ongoing plot being carried out by data plotting thread 1736 under the direction of plotting module 1534.

As shown by FIG. 22, each data processing thread 1724, 1730 consumes a maximum amount of time to process the predetermined time quantity of foundational signals, wherein this maximum amount of time to process predetermined time quantity of signals is greater than the predetermined time quantity itself. As shown by FIG. 22, by multithreading the processing of fluid parameter signals received during fluid testing, mobile analyzer 1232 serves as a mobile analyzer by processing the multiple signals being received in real time, in parallel, facilitating the plotting of the results by plotting module 1534 in real time, avoiding a reducing any lengthy delays. Processor 1510, following the instructions contained in plotting module 1534, displays the results of the data plotting thread on display 1506 while the data receiver thread 1704 is continuing to receive and buffer fluid parameter signals.

Processor 1510 further transmits data produced by data processing threads 1724, 1730, . . . 1732 across network 1500 to remote analyzer 1300. In one implementation, processor 1510 transmits the data, which comprises the results of the processing carried out in the associated data processing thread, to remote analyzer 1300 in a continuous fashion as the results of the data processing thread are generated during the execution of the data processing thread. For example, results generated at time 1740 during execution a data processing thread 1740 are immediately transferred to remote analyzer 1300 rather than waiting until time 1742 at which data processing thread 1730 has ended. In another implementation, 1510 transmits the data as a batch of data after the particular data processing thread has been completed or has ended. For example, in one implementation, processor 1510 transmits the all the results of data processing thread 1724 as a batch to remote analyzer 1300 at time 1740, the same time that such results are transmitted to data plotting thread 1736.

Processor 1602 of remote analyzer 1300, following instructions provided by memory 1604, analyzes the received data. Processor 1602 transmits the results of its analysis, the analyzed data, back to mobile analyzer 1232. Mobile analyzer 1232 displays or otherwise presents the analyzed data received from remote analyzer 1300 on display 1506 or communicates results in other fashions, whether visibly or audibly.

In one implementation, remote analyzer 1300 receives data from mobile analyzer 1232 that has already been analyzed or processed by analyzer 1232, wherein mobile analyzer 1232 has already performed or carried out some forms of manipulation of the foundational fluid parameter signals or foundational fluid parameter data received from cassette 1010. For example, in one implementation, mobile analyzer 1232 performs a first level of analysis or processing on the foundational fluid parameter data are signals. For example, impedance analysis is done on the mobile analyzer which would give the number of cells passing through the sensor. The results of such processing are then transmitted to remote analyzer 1300. Remote analyzer 1300 applies a second level of analysis or processing on the results received from mobile analyzer 1232. The second level of analysis may comprise application of additional formulas, statistical computations or the like to the results received from mobile analyzer 1232. Remote analyzer 1300 carries out additional, more complex and more time-consuming or processing power burdensome processing or analysis of the data that has already undergone some form of processing or analysis at mobile analyzer 1232. Examples of such additional analysis that is carried out at remote analyzer 1300 includes, but is not limited to, coagulation rate calculation and also analytics on data collected from various mobile analyzers to find trends and provide meaningful suggestions. For example, remote analyzer 1232 may aggregate data from several patients over a large geographic area to facilitate epidemiological studies and identify the spread of disease.

Although the present disclosure has been described with reference to example implementations, workers skilled in the art will recognize that changes may be made in form and detail without departing from the spirit and scope of the claimed subject matter. For example, although different example implementations may have been described as including features providing benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements.

What is claimed is:

1. A fluid testing system comprising:
   at least one microfluidic channel;
   a first electric sensor within a microfluidic channel to form a first electrical field within the microfluidic channel and to output a first base signal indicating an impedance of the first electrical field; and
   a second electric sensor within the microfluidic channel to form a second electrical field within the microfluidic channel and to output a second base signal indicating an impedance of the second electrical field;
   a frequency source;
   a controller to output control signals controlling the frequency source to selectively apply a first nonzero frequency of alternating current to the first electric sensor and a second, different nonzero frequency of alternating current to the second electric sensor;

a cassette comprising the at least one microfluidic channel, the first electric sensor and the second electric sensor; and a cassette interface comprising controlling hardware serving as part of the controller to control the first electric sensor and the second electric sensor, the cassette interface being releasably connected to the cassette and to be releasably connected to a portable electronic device.

2. The fluid testing system of claim 1 further comprising the portable electronic device, and an application programming interface to be stored on the portable electronic device and serving as part of the controller, wherein the application programming interface is to interface between instructions on the portable electronic device and the controlling hardware on the cassette interface.

3. The fluid testing system of claim 1, wherein the controlling hardware comprises:
a printed circuit board comprising:
the frequency source to apply the first nonzero frequency of alternating current to the first electric sensor and to apply the second nonzero frequency of alternating current to the second electric sensor;
the controller to control the frequency source;
a first impedance extractor to receive first composite signals from the first electric sensor and to extract first impedance signals from the composite signals;
a second impedance extractor to receive second composite signals from the second electric sensor and to extract second impedance signals from the second composite signals; and
a buffer to store the first and second impedance signals as the first and second impedance signals are being transmitted to an application programming interface.

4. The fluid testing system of claim 3, wherein the frequency source is selected from a group of frequency sources consisting of a direct digital synthesizer and a crystal.

5. The fluid testing system of claim 3 comprising a field programmable gate array serving as the controller and the buffer.

6. The fluid testing system of claim 3 comprising an application-specific integrated circuit serving as the controller, the first impedance extractor, the second impedance extractor and the buffer.

7. The fluid testing system of claim 1, wherein different nonzero frequencies of alternating current are applied to the first and second electric sensors so that the first and second electric sensors output different signals that indicate different properties or characteristics of a fluid in the microfluidic channel, or of cells or particles contained within a fluid in the microfluidic channel.

8. The fluid testing system of claim 7, wherein the first electric sensor is to output signals relating to a cytology test and the second electric sensor is to output signals relating to a coagulation test.

9. The fluid testing system of claim 7, wherein the first electric sensor it so output signals indicating a number of cells or particles passing across the first electric sensor, and the second electric sensor is to output signals indicating one or more characteristics of individual cells or particles passing across the second electric sensor.

10. The fluid testing system of claim 1, wherein the cassette interface is to receive electrical power from the portable electronic device.

11. A fluid testing system comprising:
controlling hardware to communicate between an application programming interface on a portable electronic device and at least one electric sensor on a fluid testing cassette, the controlling hardware comprising a printed circuit board comprising:
at least one frequency source to apply a nonzero frequency of alternating current to the at least one electric sensor;
a frequency source controller to control the at least one frequency source;
a first impedance extractor to receive base signals from the at least one electric sensor and to extract impedance signals from the base signals;
a buffer to store the impedance signals as impedance signals are being transmitted to the application programming interface; and
a cassette interface to releasably connect to the fluid testing cassette and to releasably connect to a portable electronic device, the cassette interface comprising the printed circuit board.

12. A cassette interface comprising:
a first electrical connector to releasably electrically connect directly to electrical connectors of a microfluidic cassette that includes a microfluidic channel and an electric sensor at the microfluidic channel;
a second electrical connector to releasably electrically connect directly to electrical connectors of a portable electronic device that includes a user interface, a power source, and an application programming interface;
a circuit electrically connected to the first electrical connector and the second electrical connector, the circuit to communicate power and signals between the microfluidic cassette and the portable electronic device, the circuit including firmware to carry out a test of a fluid sample in the microfluidic channel of the microfluidic cassette, the firmware to:
apply a nonzero frequency of alternating current to the electric sensor of the microfluidic cassette based on instructions originating from the application programming interface of the portable electronic device;
receive base signals from the electric sensor of the microfluidic cassette and extract impedance signals from the base signals;
buffer extracted impedance signals as buffered impedance signals; and
communicate the buffered impedance signals to the application programming interface of the portable electronic device.

13. The cassette interface of claim 12, wherein the electric sensor of the microfluidic cassette is a first electric sensor, wherein different nonzero frequencies of alternating current are applied to the first electric sensor and a second electric sensor of the microfluidic cassette so that the first and second electric sensors output different signals that indicate different properties or characteristics of a fluid in the microfluidic channel, or of cells or particles contained within a fluid in the microfluidic channel.

14. The fluid testing system of claim 13, wherein the first electric sensor is to output signals relating to a cytology test and the second electric sensor is to output signals relating to a coagulation test.

15. The fluid testing system of claim 13, wherein the first electric sensor it so output signals indicating a number of cells or particles passing across the first electric sensor, and the second electric sensor is to output signals indicating one or more characteristics of individual cells or particles passing across the second electric sensor.

\* \* \* \* \*